(12) United States Patent
Fogh et al.

(10) Patent No.: US 10,159,718 B2
(45) Date of Patent: Dec. 25, 2018

(54) PROCESS FOR PRODUCTION AND PURIFICATION OF RECOMBINANT LYSOSOMAL ALPHA-MANNOSIDASE

(71) Applicant: Chiesi Farmaceutici S.p.A., Parma (IT)

(72) Inventors: Jens Fogh, Lynge (DK); Claes Andersson, Täby (SE); Cecilia Weigelt, Stockholm (SE); Pia Hydén, Stocksund (SE); Helena Reuterwall, Solna (SE); Stefan Nilsson, Uppsala (SE)

(73) Assignee: Chiesi Farmaceutici S.p.A, Parma (IT)

( * ) Notice: Subject to any disclaimer, the term of this patent is extended or adjusted under 35 U.S.C. 154(b) by 0 days.

(21) Appl. No.: 15/619,125

(22) Filed: Jun. 9, 2017

(65) Prior Publication Data

US 2018/0036387 A1 Feb. 8, 2018

Related U.S. Application Data

(62) Division of application No. 14/635,681, filed on Mar. 2, 2015, now abandoned, which is a division of application No. 13/576,258, filed as application No. PCT/DK2011/050054 on Feb. 23, 2011, now Pat. No. 8,974,780.

(60) Provisional application No. 61/307,587, filed on Feb. 24, 2010.

(30) Foreign Application Priority Data

Feb. 24, 2010 (DK) ................................ 2010 70067

(51) Int. Cl.
- *A61K 38/00* (2006.01)
- *A61K 38/47* (2006.01)
- *C12N 9/24* (2006.01)

(52) U.S. Cl.
CPC ............ *A61K 38/47* (2013.01); *C12N 9/2488* (2013.01); *C12Y 302/01024* (2013.01); *A61K 38/00* (2013.01)

(58) Field of Classification Search
CPC ...... C12N 9/2402; A61K 38/00; A61K 38/47; C12Y 302/01024
See application file for complete search history.

(56) References Cited

U.S. PATENT DOCUMENTS

| | | | |
|---|---|---|---|
| 5,705,364 A * | 1/1998 | Etcheverry ...... | C07K 14/70503 435/375 |
| 7,507,573 B2 | 3/2009 | Contreras et al. | |
| 2003/0199073 A1* | 10/2003 | Fogh .............. | C12Y 302/01024 435/200 |
| 2004/0053235 A1 | 3/2004 | Smirnoff et al. | |
| 2009/0191178 A1 | 7/2009 | Zankel et al. | |

FOREIGN PATENT DOCUMENTS

| | | |
|---|---|---|
| CN | 1298862 A | 6/2001 |
| CN | 101085345 A | 12/2007 |
| CN | 101410408 A | 4/2009 |
| EP | 1 408 117 A1 | 4/2004 |
| JP | 5-252977 | 10/1993 |
| JP | 2007-523648 | 8/2007 |
| JP | 2009532394 | 9/2009 |
| KR | 20010070144 A | 7/2001 |
| WO | WO 02/15927 A1 | 2/2002 |
| WO | WO 02/099092 A2 | 12/2002 |
| WO | WO 2005/073367 A1 | 8/2005 |
| WO | WO 2005/077093 A2 | 8/2005 |
| WO | WO 2005/094874 A1 | 10/2005 |
| WO | WO 2007/112757 A2 | 10/2007 |
| WO | WO 2009/007451 A1 | 1/2009 |

OTHER PUBLICATIONS

Aronsen N.N et al., "Lysosonal degradation of Asn-linked glycoproteins", FASEB J, 1989, pp. 2615-2622, vol. 3.
Barton N.W et al.; "Replacement Therapy for Inherited Enzyme Deficiency—Macrophage-Targeted Glucocerebrosidase for Gaucher's Disease", N Engl J Med, 1991, pp. 1464-1470, vol. 324.
Berg T et al.; "Purification and characterization of recombinant human lysosomal alpha-mannosidase", Molecular Genetics and Metabolism, 2001, pp. 18-29, vol. 73.
Berg T et al., "Purification of feline lysosomal alpha-mannosidase, determination of its cDNA sequence and identification of a mutation causing alpha-mannosidosis in Persian cats", Biochem J, 1997, pp. 863-870, vol. 328.
Blanz J et al., "Reversal of peripheral and central neural storage and ataxia after recombinant enzyme replacement therapy in alpha-mannosidosis mice", Human Molecular Genetics, 2008, pp. 3437-3445, vol. 17(22).
Blast Sequence Comparison of SEQ ID No. 2 and alpha-mannosidase of Contreras (U.S. Pat. No. 7,507,573), accessed at http://blast.ncbi/nlm.nih.gov/Blast.cgi on Sep. 16, 2013.
Blast Sequence Comparison of SEQ ID No. 2 and alpha-mannosidase of Riviera-Marrero (Microbial Pathology 2001), accessed at http://blast.ncbi/nlm.nih.gov/Blast.cgi on Sep. 16, 2013.
Chen J et al., "The distinctive separation attributes of mixed-mode resins and their application in monoclonal antibody downstream purification process", Journal of Chromatography, 2010, pp. 216-224, vol. 1217.
Crawley A et al., "alpha-Mannosidosis in the guinea pig: A new animal model for lysosomal storage disorders", Pediatr Res, 1999, pp. 501-509, vol. 46.
Crawley A et al. "Enzyme replacement therapy in alpha-mannosidosis guinea-pigs", Molecular Genetics and Metabolism, 2006, pp. 48-57, vol. 89.

(Continued)

*Primary Examiner* — Maryam Monshipouri
(74) *Attorney, Agent, or Firm* — Knobbe Martens Olson & Bear LLP

(57) ABSTRACT

The present invention relates to a process for purification of recombinant alpha-mannosidase, a process for production of alpha-mannosidase, a composition comprising alpha-mannosidase, use of the composition as a medicament, use as a medicament for the treatment of alpha-mannosidosis and a method of treating alpha-mannosidosis and/or alleviating the symptoms of alpha-mannosidosis.

13 Claims, 9 Drawing Sheets

Specification includes a Sequence Listing.

(56) References Cited

OTHER PUBLICATIONS

Forsee W.T. et al., "Purification and characterization of an alpha-1,2-mannosidase involved in processing asparagine-linked oligosaccharides", Journal of Biological Chemistry, 1989, pp. 3869-3876, vol. 264, No. 7.

Gallant et al., "Dye Ligand Chromatography" (2008) Methods in Molecular Biology: vol. 421: Affinity Chromatography: Methods and Protocols, Second Edition, p. 61-69.

GE Healthcare, Capto MMC, 2005, [searched: Feb. 2, 2016], URL,http://wolfson.huji.ac.il/purification/PDF/IonExchange/AMERSHAM_CAPTO_MMC.pdf.

Guofeng Z et al., "Ligands for mixed-mode protein chromatography: Principles, characteristics and design", Journal of Biotechnology, 2009, pp. 3-11, vol. 144.

Grubb J:H. et al., "Chemically modified-glucuronidase crosses blood-brain barrier and clears neuronal storage in murine mucopolysaccharidosis VII", PNAS, 2008, pp. 2616-2621. vol. 105(7).

Hansen G. et al., "Intracellular transport of human lysosomal alpha-mannosidase and alpha-mannosidosis related mutants", Biochem J, 2004, pp. 537-567, vol. 381.

Heikinheimo P. et al., "The structure of bovine lysosomal alpha-mannosidase suggests a novel mechanism for low-pH activation", J Mol Biol, 2003, pp. 631-644, vol. 327, Abstract.

Hirsch C. et al., "A role for N-glucanase in the cytosolic turnover of glycoproteins", EMBO J., 2003, pp. 1036-1046, vol. 22.

"His Bind Kits" (2005) Novagen, 1-20.

Hocking J.D. et al., "Deficiency in alpha-mannosidase in angus cattle", Biochem J, 1972, pp. 69-78, vol. 128.

Jenkins, Nigel, and Elisabeth MA Curling. "Glycosylation of recombinant proteins: problems and prospects." Enzyme and microbial technology 16.5 (1994): 354-364.

Journal of Chromatography A, 1988, vol. 435, pp. 127-137.

Kaneda Y. et al., "Reginal assignment of five genes on chromosome 19", Chromosoma, 1987, pp. 8-12, vol. 95.

Liao Y.F. et al., "Cloning, expression, purification, and characterization of the human broad specificity lysosomal acid alpha-mannosidase", J Biol Chem, 1996, pp. 28348-28358, vol. 271.

Lal, et al., "Substrate specificities of recombinant murine Golgi α1,2-mannosidases IA and IB and comparison with endoplasmic reticulum and Golgi processing α 1,2-,annosidases," Glycobiology, 1998, vol. 8, p. 981-995.

Nebes V.L. et al., "Human lysosomal alpha-mannosidase: Isolation and nucleotide sequence of the full length cDNA", Biochem. Biophys. res. Commun., 1994, pp. 239-245, vol. 200.

Nilssen Ø et al., "Alpha-Mannosidosis: functional cloning of the lysosomal alpha-mannosidase cDNA and identification of a mutation in two affected siblings", Hum. Mol. Genet., 1997, pp. 717-726, vol. 6.

Prows C.A. et al., "Gaucher disease: enzyme therapy in the acute neuronopathic variant", Am J Med Genet, 1997, pp. 16-21, vol. 71, Abstract.

Riise H.M.F. et al., "Genomic structure of the human lysosomal alpha-mannosidase gene (MANB)", Genomics, 1997, pp. 200-2007, vol. 42.

Rivera-Marrero et al., "Molecular cloning and expression of an alpha-mannosidase gene in *Mycobacterium tuberculosis.*" (2001) Microbial Pathogenesis, vol. 30: 9-18.

Roces D.P. et al., "Efficacy of enzyme replacement therapy in alpha-mannosidosis mice: a preclinical animal study", Human Molecular Genetics, 2004, pp. 1979-1988, vol. 13(18).

Saint Pol A. et al., "Cytosol-to-lysosome transport of free polymannose-type oligosaccharides", J Biol Chem, 1999, pp. 13547-13555, vol. 274.

Sakuraba, Hitoshi, et al. "Comparison of the effects of agalsidase alfa and agalsidase beta on cultured human Fabry fibroblasts and Fabry mice." Journal of human genetics 51.3 (2006): 180-188.

Stinchi S. et al., "Targeted disruption of the lysosomal alpha-mannosidase gene results in mice resembling a mild form of human alpha-mannosidosis", Hum Mol Genet, 1999, pp. 1366-1372, vol. 8.

Tollersrud O.K. et al., "Purification of bovine lysosomal alpha-mannosidase, characterization of its gene and determination of two mutations that cause alpha-mannosidosis", Eur J Biochem, 1997, pp. 410-419, vol. 246.

Venkatesan et al., "Human lysosomal alpha-mannosidases exhibit different inhibition and metal binding proeprties." (Aug. 2009) Protein Science, vol. 18: 2242-2251.

Walkley S.U. et al., "Bone marrow transplantation corrects the enzyme defect in neurons of the central nervous system in a lysosomal storage disease", PNAS, 1994, pp. 2970-2974, vol. 91.

Will A. et al., "Bone marrow transplantation in the treatment of alpha-mannosidosis", Arch Dis Child, 1987, pp. 1044-1049, vol. 62(10), Abstract.

* cited by examiner

SEQUENCE LISTING

<160> NUMBER OF SEQ ID NOS: 2

<210> SEQ ID NO 1
<211> LENGTH: 8079
<212> TYPE: DNA
<213> ORGANISM: Artificial
<220> FEATURE:
<223> OTHER INFORMATION: Expression plasmid pLamanExp1

<400> SEQUENCE: 1

| | | | | | | |
|---|---|---|---|---|---|---|
| agatcttcaa | tattggccat | tagccatatt | attcattggt | tatatagcat | aaatcaatat | 60 |
| tggctattgg | ccattgcata | cgttgtatct | atatcataat | atgtacattt | atattggctc | 120 |
| atgtccaata | tgaccgccat | gttggcattg | attattgact | agttattaat | agtaatcaat | 180 |
| tacgggtca | ttagttcata | gcccatatat | ggagttccgc | gttacataac | ttacggtaaa | 240 |
| tggcccgcct | ggctgaccgc | ccaacgaccc | ccgcccattg | acgtcaataa | tgacgtatgt | 300 |
| tcccatagta | acgccaatag | ggactttcca | ttgacgtcaa | tgggtggagt | atttacggta | 360 |
| aactgcccac | ttggcagtac | atcaagtgta | tcatatgcca | agtccgcccc | ctattgacgt | 420 |
| caatgacggt | aaatggcccg | cctggcatta | tgcccagtac | atgaccttac | gggactttcc | 480 |
| tacttggcag | tacatctacg | tattagtcat | cgctattacc | atggtgatgc | ggttttggca | 540 |
| gtacaccaat | gggcgtggat | agcggtttga | ctcacgggga | tttccaagtc | tccaccccat | 600 |
| tgacgtcaat | gggagtttgt | tttggcacca | aaatcaacgg | gactttccaa | aatgtcgtaa | 660 |
| caactgcgat | cgcccgcccc | gttgacgcaa | atgggcggta | ggcgtgtacg | gtgggaggtc | 720 |
| tatataagca | gagctcgttt | agtgaaccgt | cagatcacta | gaagctttat | gcggtagtt | 780 |
| tatcacagtt | aaattgctaa | cgcagtcagt | gcttctgaca | acagtctc | gaacttaagc | 840 |
| tgcagtgact | ctcttaaggt | agccttgcag | aagttggtcg | tgaggcactg | gcaggtaag | 900 |
| tatcaaggtt | acaagacagg | tttaaggaga | ccaatagaaa | ctgggcttgt | cgagacagag | 960 |
| aagactcttg | cgtttctgat | aggcacctat | tggtcttact | gacatccact | ttgcctttct | 1020 |
| ctccacaggt | gtccactccc | agttcaatta | cagctcttaa | ggctagagta | cttaatacga | 1080 |
| ctcactatag | gctagcctcg | agaattcgcc | gccatgggcg | cctacgcgcg | ggcttcgggg | 1140 |
| gtctgcgctc | gaggctgcct | ggactcagca | ggccctgga | ccatgtcccg | cgccctgcgg | 1200 |
| ccaccgctcc | cgcctctctg | ctttttcctt | ttgttgctgg | cggctgccgg | tgctcgggcc | 1260 |
| ggggatacg | agacatgccc | cacagtgcag | ccgaacatgc | tgaacgtgca | cctgctgcct | 1320 |
| cacacacatg | atgacgtggg | ctggctcaaa | accgtggacc | agtacttta | tggaatcaag | 1380 |
| aatgacatcc | agcacgccgg | tgtgcagtac | atcctggact | cggtcatctc | tgccttgctg | 1440 |
| gcagatccca | cccgtcgctt | catttacgtg | gagattgcct | tcttctcccg | ttggtggcac | 1500 |
| cagcagacaa | atgccacaca | ggaagtcgtg | cgagaccttg | tgcgccaggg | gcgcctggag | 1560 |
| ttcgccaatg | gtgctgggt | gatgaacgat | gaggcagcca | cccactacgg | tgccatcgtg | 1620 |
| gaccagatga | cacttgggct | gcgctttctg | gaggacacat | ttggcaatga | tgggcgaccc | 1680 |
| cgtgtggcct | ggcacattga | ccccttcggc | cactctcggg | agcaggcctc | gctgtttgcg | 1740 |
| cagatgggct | cgacggctt | cttctttggg | cgccttgatt | atcaagataa | gtgggtacgg | 1800 |
| atgcagaagc | tggagatgga | gcaggtgtgg | cgggccagca | ccagcctgaa | gcccccgacc | 1860 |
| gcggacctct | tcactggtgt | gcttcccaat | ggttacaacc | cgccaaggaa | tctgtgctgg | 1920 |
| gatgtgctgt | gtgtcgatca | gccgctggtg | gaggaccctc | gcagcccga | gtacaacgcc | 1980 |
| aaggagctgg | tcgattactt | cctaaatgtg | gccactgccc | agggccggta | ttaccgcacc | 2040 |

```
aaccacactg tgatgaccat gggctcggac ttccaatatg agaatgccaa catgtggttc    2100
aagaaccttg acaagctcat ccggctggta aatgcgcagc aggcaaaagg aagcagtgtc    2160
catgttctct actccacccc cgcttgttac ctctgggagc tgaacaaggc caacctcacc    2220
tggtcagtga aacatgacga cttcttccct tacgcggatg cccccacca gttctggacc    2280 ggttactttt ccagtcggcc ggccctcaaa cgctacgagc gcctcagcta caacttcctg    2340
caggtgtgca accagctgga ggcgctgtg ggcctggcgg ccaacgtggg accctatggc    2400
tccggagaca gtgcacccct caatgaggcg atggctgtgc tccagcatca cgacgccgtc    2460
agcggcacct cccgccagca cgtggccaac gactacgcgc ccagcttgc ggcaggctgg    2520 gggccttgcg aggttcttct gagcaacgcg ctggcgcggc tcagaggctt caaagatcac    2580 ttcaccttt gccaacagct aaacatcagc atctgcccgc tcagccagac ggcggcgcgc    2640
ttccaggtca tcgtttataa tccccctggg cggaaggtga attggatggt acggctgccg    2700
gtcagcgaag gcgttttcgt tgtgaaggac cccaatggca ggacagtgcc cagcgatgtg    2760
gtaatatttc ccagctcaga cagccaggcg caccctccgg agctgctgtt ctcagcctca    2820
ctgcccgccc tgggcttcag cacctattca gtagcccagg tgcctcgctg aagcccag    2880 gcccgcgcac cacagcccat ccccagaaga tcctggtccc ctgctttaac catcgaaaat    2940
gagcacatcc gggcaacgtt tgatcctgac acagggctgt tgatggagat tatgaacatg    3000
aatcagcaac tcctgctgcc tgttcgccag accttcttct ggtacaacgc cagtataggt    3060
gacaacgaaa gtgaccaggc ctcaggtgcc tacatcttca gacccaacca acagaaaccg    3120
ctgcctgtga gccgctgggc tcagatccac ctggtgaaga caccttggt gcaggaggtg    3180 caccagaact tctcagcttg gtgttccag gtggttcgcc tgtacccagg acagcggcac    3240
ctggagctag agtggtcggt ggggccgata cctgtgggcg cacctgggg aaggaggtc    3300 atcagccgtt ttgacacacc gctggagaca aagggacgct tctacacaga cagcaatggc    3360
cgggagatcc tggagaggag gcgggattat cgacccacct ggaaactgaa ccagacggag    3420
cccgtggcag gaaactacta tccagtcaac acccggattt acatcacgga tggaaacatg    3480
cagctgactg tgctgactga ccgctcccag gggggcagca gcctgagaga tggctcgctg    3540
gagctcatgg tgcaccgaag gctgctgaag gacgatggac gcggagtatc ggagccacta    3600
atggagaacg gtcggggc gtgggtgcga gggcgccacc tggtgctgct ggacacagcc    3660
caggctgcag ccgccggaca ccggctcctg gcggagcagg aggtcctggc ccctcaggtg    3720
gtgctggccc cgggtggcgg cgccgcctac aatctcgggg ctcctccgcg cacgcagttc    3780
tcagggctgc gcaggaccct gccgccctcg gtgcacctgc tcacgctggc cagctgggc    3840 cccgaaatgt gctgctgcg cttggagcac cagtttgccg taggagagga ttccggacgt    3900
aacctgagcg ccccgttac cttgaacttg agggacctgt tctccacctt caccatcacc    3960
cgcctgcagg agaccacgct ggtggccaac cagctccgcg aggcagcctc caggctcaag    4020
tggacaacaa acacaggccc cacacccac caaactccgt accagctgga cccggccaac    4080
atcacgctgg aacccatgga aatccgcact ttcctggcct cagttcaatg gaaggaggtg    4140
gatggttagg tctgctggga tgggccctct agagtcgacc cggcggccg cttccctta    4200 gtgagggtta atgcttcgag cagacatgat aagatacatt gatgagtttg gacaaaccac    4260
aactagaatg cagtgaaaaa aatgctttat ttgtgaaatt tgtgatgcta ttgctttatt    4320
tgtaaccatt ataagctgca ataaacaagt taacaacaac aattgcattc attttatgtt    4380
```

```
tcaggttcag ggggagatgt gggaggtttt ttaaagcaag taaaacctct acaaatgtgg    4440
taaaatccga taaggatcga tccgggctgg cgtaatagcg aagaggcccg caccgatcgc    4500
ccttcccaac agttgcgcag cctgaatggc gaatggacgc gccctgtagc ggcgcattaa    4560
gcgcggcggt tgtggtggtt acgcgcagcg tgaccgctac acttgccagc gccctagcgc    4620
ccgctccttt cgctttcttc ccttcctttc tcgccacgtt cgccggcttt cccgtcaag    4680 ctctaaatcg ggggctccct ttaggggttcc gatttagagc tttacggcac ctcgaccgca    4740
aaaaacttga tttgggtgat ggttcacgta gtgggccatc gccctgatag acggttttc    4800 gcccttgac gttggagtcc acgttcttta atagtggact cttgttccaa actggaacaa    4860
cactcaaccc tatctcggtc tattcttttg atttataagg gatttgggg atttcggcct    4920 attggttaaa aaatgagctg atttaacaaa aatttaacgc gaattaattc tgtggaatgt    4980
gtgtcagtta gggtgtggaa agtccccagg ctccccaggc aggcagaagt atgcaaagca    5040
tgcatctcaa ttagtcagca accaggtgtg gaaagtcccc aggctcccca gcaggcagaa    5100
gtatgcaaag catgcatctc aattagtcag caaccatagt cccgcccta actccgccca    5160 tcccgcccct aactccgccc agttccgccc attctccgcc ccatggctga ctaattttt    5220 ttatttatgc agaggccgag gccgcctctg cctctgagct attccagaag tagtgaggag    5280
gcttttttgg aggcctaggc ttttgcaaaa agctcccggg atggttcgac cattgaactg    5340
catcgtcgcc gtgtcccaaa atatgggat tggcaagaac ggagacctac cctggcctcc    5400
gctcaggaac gagttcaagt acttccaaag aatgaccaca acctcttcag tggaaggtaa    5460
acagaatctg gtgattatgg gtaggaaaac ctggttctcc attcctgaga gaatcgacc    5520 tttaaggac agaattaata tagttctcag tagagaactc aaagaaccac cacgaggagc    5580
tcattttctt gccaaaagtt tggatgatgc cttaagactt attgaacaac cggaattggc    5640
aagtaaagta gacatggttt ggatagtcgg aggcagttct gtttaccagg aagccatgaa    5700
tcaaccaggc caccctagac tctttgtgac aaggatcatg caggaatttg aaagtgacac    5760 gttttttccca gaaattgatt tggggaaata taaacttctc ccagaatacc caggcgtcct    5820
ctctgaggtc caggaggaaa aaggcatcaa gtataagttt gaagtctacg agaagaaaga    5880
ctaattcgaa atgaccgacc aagcgacgcc caacctgcca tcacgatggc cgcaataaaa    5940
tatctttatt ttcattacat ctgtgtgttg gttttttgtg tgaatcgata gcgataagga    6000
tccgcgtatg gtgcactctc agtacaatct gctctgatgc cgcatagtta agccagcccc    6060
gacacccgcc aacacccgct gacgcgccct gacgggcttg tctgctcccg gcatccgctt    6120
acagacaagc tgtgaccgtc tccgggagct gcatgtgtca gaggttttca ccgtcatcac    6180
cgaaacgcgc gagacgaaag gcctcgtga tacgcctatt tttataggtt aatgtcatga    6240
taataatggt ttcttagacg tcaggtggca cttttcgggg aaatgtgcgc ggaacccta    6300 tttgtttatt tttctaaata cattcaaata tgtatccgct catgagacaa taaccctgat    6360
aaatgcttca ataatattga aaaggaaga gtatgagtat tcaacatttc cgtgtcgccc    6420
ttattccctt ttttgcggca ttttgccttc ctgtttttgc tcacccagaa acgctggtga    6480
aagtaaaaga tgctgaagat cagttgggtg cacgagtggg ttacatcgaa ctggatctca    6540
acagcggtaa gatccttgag agttttcgcc ccgaagaacg ttttccaatg atgagcactt    6600
ttaaagttct gctatgtggc gcggtattat cccgtattga cgccgggcaa gagcaactcg    6660
gtcgccgcat acactattct cagaatgact tggttgagta ctcaccagtc acagaaaagc    6720
atcttacgga tggcatgaca gtaagagaat tatgcagtgc tgccataacc atgagtgata    6780
```

-continued

```
acactgcggc caacttactt ctgacaacga tcggaggacc gaaggagcta accgcttttt     6840
tgcacaacat gggggatcat gtaactcgcc ttgatcgttg gaaccggag  ctgaatgaag     6900
ccataccaaa cgacgagcgt gacaccacga tgcctgtagc aatggcaaca acgttgcgca     6960
aactattaac tggcgaacta cttactctag cttcccggca acaattaata gactggatgg     7020
aggcggataa agttgcagga ccacttctgc gctcggccct tccggctggc tggtttattg     7080
ctgataaatc tggagccggt gagcgtgggt ctcgcggtat cattgcagca ctggggccag     7140
atggtaagcc ctcccgtatc gtagttatct acacgacggg gagtcaggca actatggatg     7200
aacgaaatag acagatcgct gagataggtg cctcactgat taagcattgg taactgtcag     7260
accaagttta ctcatatata ctttagattg atttaaaact tcattttaa  tttaaaagga     7320
tctaggtgaa gatccttttt gataatctca tgaccaaaat cccttaacgt gagttttcgt     7380
tccactgagc gtcagacccc gtagaaaaga tcaaaggatc ttcttgagat ccttttttc      7440
tgcgcgtaat ctgctgcttg caaacaaaaa aaccaccgct accagcggtg gtttgtttgc     7500
cggatcaaga gctaccaact cttttccga  aggtaactgg cttcagcaga gcgcagatac     7560
caaatactgt ccttctagtg tagccgtagt taggccacca cttcaagaac tctgtagcac     7620
cgcctacata cctcgctctg ctaatcctgt taccagtggc tgctgccagt ggcgataagt     7680
cgtgtcttac cgggttggac tcaagacgat agttaccgga taaggcgcag cggtcgggct     7740
gaacggggg  ttcgtgcaca cagcccagct tggagcgaac gacctacacc gaactgagat     7800
acctacagcg tgagctatga gaaagcgcca cgcttcccga agggagaaag gcggacaggt     7860
atccggtaag cggcagggtc ggaacaggag agcgcacgag ggagcttcca gggggaaacg     7920
cctggtatct ttatagtcct gtcgggttc  gccacctctg acttgagcgt cgatttttgt     7980
gatgctcgtc aggggggcgg agcctatgga aaaacgccag caacgcggcc ttttacggt      8040
tcctggcctt tgctggcct  tttgctcaca tggctcgac                            8079
```

<210> SEQ ID NO 2
<211> LENGTH: 1011
<212> TYPE: PRT
<213> ORGANISM: Homo sapiens

<400> SEQUENCE: 2

```
Met Gly Ala Tyr Ala Arg Ala Ser Gly Val Cys Ala Arg Gly Cys Leu
1               5                   10                  15

Asp Ser Ala Gly Pro Trp Thr Met Ser Arg Ala Leu Arg Pro Pro Leu
            20                  25                  30

Pro Pro Leu Cys Phe Phe Leu Leu Leu Ala Ala Ala Gly Ala Arg
        35                  40                  45

Ala Gly Gly Tyr Glu Thr Cys Pro Thr Val Gln Pro Asn Met Leu Asn
    50                  55                  60

Val His Leu Leu Pro His Thr His Asp Asp Val Gly Trp Leu Lys Thr
65                  70                  75                  80

Val Asp Gln Tyr Phe Tyr Gly Ile Lys Asn Asp Ile Gln His Ala Gly
                85                  90                  95

Val Gln Tyr Ile Leu Asp Ser Val Ile Ser Ala Leu Leu Ala Asp Pro
            100                 105                 110

Thr Arg Arg Phe Ile Tyr Val Glu Ile Ala Phe Phe Ser Arg Trp Trp
        115                 120                 125

His Gln Gln Thr Asn Ala Thr Gln Glu Val Val Arg Asp Leu Val Arg
    130                 135                 140
```

```
Gln Gly Arg Leu Glu Phe Ala Asn Gly Gly Trp Val Met Asn Asp Glu
145                 150                 155                 160

Ala Ala Thr His Tyr Gly Ala Ile Val Asp Gln Met Thr Leu Gly Leu
            165                 170                 175

Arg Phe Leu Glu Asp Thr Phe Gly Asn Asp Gly Arg Pro Arg Val Ala
            180                 185                 190

Trp His Ile Asp Pro Phe Gly His Ser Arg Glu Gln Ala Ser Leu Phe
            195                 200                 205

Ala Gln Met Gly Phe Asp Gly Phe Phe Gly Arg Leu Asp Tyr Gln
210                 215                 220

Asp Lys Trp Val Arg Met Gln Lys Leu Glu Met Glu Gln Val Trp Arg
225                 230                 235                 240

Ala Ser Thr Ser Leu Lys Pro Thr Ala Asp Leu Phe Thr Gly Val
            245                 250                 255

Leu Pro Asn Gly Tyr Asn Pro Arg Asn Leu Cys Trp Asp Val Leu
            260                 265                 270

Cys Val Asp Gln Pro Leu Val Glu Asp Pro Arg Ser Pro Glu Tyr Asn
            275                 280                 285

Ala Lys Glu Leu Val Asp Tyr Phe Leu Asn Val Ala Thr Ala Gln Gly
290                 295                 300

Arg Tyr Tyr Arg Thr Asn His Thr Val Met Thr Met Gly Ser Asp Phe
305                 310                 315                 320

Gln Tyr Glu Asn Ala Asn Met Trp Phe Lys Asn Leu Asp Lys Leu Ile
            325                 330                 335

Arg Leu Val Asn Ala Gln Gln Ala Lys Gly Ser Ser Val His Val Leu
            340                 345                 350

Tyr Ser Thr Pro Ala Cys Tyr Leu Trp Glu Leu Asn Lys Ala Asn Leu
            355                 360                 365

Thr Trp Ser Val Lys His Asp Asp Phe Phe Pro Tyr Ala Asp Gly Pro
370                 375                 380

His Gln Phe Trp Thr Gly Tyr Phe Ser Ser Arg Pro Ala Leu Lys Arg
385                 390                 395                 400

Tyr Glu Arg Leu Ser Tyr Asn Phe Leu Gln Val Cys Asn Gln Leu Glu
            405                 410                 415

Ala Leu Val Gly Leu Ala Ala Asn Val Gly Pro Tyr Gly Ser Gly Asp
            420                 425                 430

Ser Ala Pro Leu Asn Glu Ala Met Ala Val Leu Gln His His Asp Ala
            435                 440                 445

Val Ser Gly Thr Ser Arg Gln His Val Ala Asn Asp Tyr Ala Arg Gln
            450                 455                 460

Leu Ala Ala Gly Trp Gly Pro Cys Glu Val Leu Leu Ser Asn Ala Leu
465                 470                 475                 480

Ala Arg Leu Arg Gly Phe Lys Asp His Phe Thr Phe Cys Gln Gln Leu
            485                 490                 495

Asn Ile Ser Ile Cys Pro Leu Ser Gln Thr Ala Ala Arg Phe Gln Val
            500                 505                 510

Ile Val Tyr Asn Pro Leu Gly Arg Lys Val Asn Trp Met Val Arg Leu
            515                 520                 525

Pro Val Ser Glu Gly Val Phe Val Val Lys Asp Pro Asn Gly Arg Thr
            530                 535                 540

Val Pro Ser Asp Val Val Ile Phe Pro Ser Ser Asp Ser Gln Ala His
545                 550                 555                 560
```

-continued

Pro Pro Glu Leu Leu Phe Ser Ala Ser Leu Pro Ala Leu Gly Phe Ser
                565                 570                 575

Thr Tyr Ser Val Ala Gln Val Pro Arg Trp Lys Pro Gln Ala Arg Ala
            580                 585                 590

Pro Gln Pro Ile Pro Arg Arg Ser Trp Ser Pro Ala Leu Thr Ile Glu
            595                 600                 605

Asn Glu His Ile Arg Ala Thr Phe Asp Pro Asp Thr Gly Leu Leu Met
            610                 615                 620

Glu Ile Met Asn Met Asn Gln Gln Leu Leu Leu Pro Val Arg Gln Thr
625                 630                 635                 640

Phe Phe Trp Tyr Asn Ala Ser Ile Gly Asp Asn Glu Ser Asp Gln Ala
                645                 650                 655

Ser Gly Ala Tyr Ile Phe Arg Pro Asn Gln Gln Lys Pro Leu Pro Val
                660                 665                 670

Ser Arg Trp Ala Gln Ile His Leu Val Lys Thr Pro Leu Val Gln Glu
            675                 680                 685

Val His Gln Asn Phe Ser Ala Trp Cys Ser Gln Val Val Arg Leu Tyr
            690                 695                 700

Pro Gly Gln Arg His Leu Glu Leu Glu Trp Ser Val Gly Pro Ile Pro
705                 710                 715                 720

Val Gly Asp Thr Trp Gly Lys Glu Val Ile Ser Arg Phe Asp Thr Pro
                725                 730                 735

Leu Glu Thr Lys Gly Arg Phe Tyr Thr Asp Ser Asn Gly Arg Glu Ile
                740                 745                 750

Leu Glu Arg Arg Arg Asp Tyr Arg Pro Thr Trp Lys Leu Asn Gln Thr
            755                 760                 765

Glu Pro Val Ala Gly Asn Tyr Tyr Pro Val Asn Thr Arg Ile Tyr Ile
770                 775                 780

Thr Asp Gly Asn Met Gln Leu Thr Val Leu Thr Asp Arg Ser Gln Gly
785                 790                 795                 800

Gly Ser Ser Leu Arg Asp Gly Ser Leu Glu Leu Met Val His Arg Arg
                805                 810                 815

Leu Leu Lys Asp Asp Gly Arg Gly Val Ser Glu Pro Leu Met Glu Asn
                820                 825                 830

Gly Ser Gly Ala Trp Val Arg Gly Arg His Leu Val Leu Leu Asp Thr
            835                 840                 845

Ala Gln Ala Ala Ala Ala Gly His Arg Leu Leu Ala Glu Gln Glu Val
            850                 855                 860

Leu Ala Pro Gln Val Val Leu Ala Pro Gly Gly Gly Ala Ala Tyr Asn
865                 870                 875                 880

Leu Gly Ala Pro Pro Arg Thr Gln Phe Ser Gly Leu Arg Arg Asp Leu
                885                 890                 895

Pro Pro Ser Val His Leu Leu Thr Leu Ala Ser Trp Gly Pro Glu Met
            900                 905                 910

Val Leu Leu Arg Leu Glu His Gln Phe Ala Val Gly Glu Asp Ser Gly
            915                 920                 925

Arg Asn Leu Ser Ala Pro Val Thr Leu Asn Leu Arg Asp Leu Phe Ser
930                 935                 940

Thr Phe Thr Ile Thr Arg Leu Gln Glu Thr Thr Leu Val Ala Asn Gln
945                 950                 955                 960

Leu Arg Glu Ala Ala Ser Arg Leu Lys Trp Thr Thr Asn Thr Gly Pro
                965                 970                 975

Thr Pro His Gln Thr Pro Tyr Gln Leu Asp Pro Ala Asn Ile Thr Leu

```
            980             985             990
Glu Pro Met Glu Ile Arg Thr Phe Leu Ala Ser Val Gln Trp Lys Glu
        995                 1000                1005

Val Asp Gly
    1010
```

PROCESS FOR PRODUCTION AND PURIFICATION OF RECOMBINANT LYSOSOMAL ALPHA-MANNOSIDASE

CROSS REFERENCE TO RELATED APPLICATIONS

This application is a divisional application of U.S. application Ser. No. 14/635,681, filed Mar. 2, 2015, which is a divisional application of U.S. application Ser. No. 13/576,258, filed on Jul. 31, 2012, which is a U.S. National Phase Application of PCT International Application Number PCT/DK2011/050054, filed on Feb. 23, 2011, designating the United States of America and published in the English language, which is an International Application of and claims the benefit of priority to U.S. Provisional Application No. 61/307,587, filed on Feb. 24, 2010, and Danish Patent Application No. PA 2010 70067, filed on Feb. 24, 2010. The disclosures of the above-referenced applications are hereby expressly incorporated by reference in their entireties.

FIELD OF THE INVENTION

The present invention relates to a process for purification of recombinant alpha-mannosidase, a process for production of alpha-mannosidase, a composition comprising alpha-mannosidase, use of the composition as a medicament, use as a medicament for the treatment of alpha-mannosidosis and a method of treating alpha-mannosidosis and/or alleviating the symptoms of alpha-mannosidosis.

Alpha-Mannosidosis

Alpha-mannosidosis is a recessive, autosomal disease that occurs world wide with a frequency of between $1/1,000,000$ and $1/500,000$. Mannosidosis is found in all ethnic groups in Europe, America, Africa and also Asia. It is detected in all countries with a good diagnostic service for lysosomal storage disorders, at a similar frequency. They are born apparently healthy, however the symptoms of the diseases are progressive. Alpha-mannosidosis displays clinical heterogeneity, ranging from very serious to very mild forms. Typical clinical symptoms are: mental retardation, skeletal changes, impaired immune system resulting in recurrent infections, hearing impairment and often the disease is associated with a typical facial characteristics such as a coarse face, a prominent forehead, a flattened nasal bridge, a small nose, and a broad mouth. In the most severe cases (mannosidosis type I) the children suffer from hepatosplenomegaly, and they die during the first years of life. Possibly this early death is caused by severe infections due to the immunodeficiency caused by the disease. In milder cases (mannosidosis type 2) the patients usually reach adult age. The skeletal weaknesses of the patients result in the needs of wheeling chairs at age 20 to 40. The disease causes a diffuse dysfunction of the brain often resulting in weak mental performances that excludes anything but the most basic skills of simple reading and writing. These problems associated with hearing inabilities and other clinical manifestations preclude the patient from an independent life, the consequence being that lifelong caretaking is needed.

Lysosomal Alpha-Mannosidase

Alpha-mannosidosis results from a deficient activity of lysosomal alpha-mannosidase (LAMAN, EC3.2.1.24). The disease is characterised by massive intracellular accumulation of mannose-rich oligosaccharides, that is oligosaccharides carrying α1,2-, α1,3- and α1,6-mannosyl residues at their non-reducing termini. These oligosaccharides mainly originate from the intralysosomal degradation of glycoproteins with N-linked oligosaccharides. However, some originate from the catabolism of dolichol-linked oligosaccharides and from misfolded glycoproteins redirected to the cytosol for degradation by the proteasome (Hirsch et al. EMBO J. 22, 1036-1046, 2003 and Saint-Pol et al. J. Biol. Chem. 274, 13547-13555, 1999). The lysosomal storage is observed in a wide range of cell types and tissues, including neurons in all brain regions. LAMAN is an exoglycosidase which hydrolyses these terminal, non-reducing alpha-D-mannose residues in alpha-D-mannosides from the non-reducing end during the ordered degradation of the N-linked glycoproteins (Aronson and Kuranda FASEB J 3:2615-2622. 1989). The human precursor enzyme is synthesised as a single polypeptide of 1011 amino acids including a signal peptide of 49 residues. The precursor is proteolytically processed into three main glycopeptides of 15, 42, and 70 kD to the matured enzyme in the lysosome. The 70 kD glycopeptide is further processed into three subunits linked by disulfide bridges. (Berg et al. Mol. Gen. and Metabolism 73, 18-29, 2001, Nilssen et al. Hum. Mol. Genet. 6, 717-726. 1997).

The Lysosomal Alpha-Mannosidase Gene

The gene coding for LAMAN (MANB) is located at chromosome 19 (19cen-q12), (Kaneda et al. Chromosoma 95:8-12. 1987). MANB consists of 24 exons, spanning 21.5 kb (GenBank accession numbers U60885-U60899; Riise et al. Genomics 42:200-207, 1997). The LAMAN transcript is >>3,500 nucleotides (nts) and contains an open reading frame encoding 1,011 amino acids (GenBank U60266.1). The cloning and sequencing of the human cDNA encoding LAMAN has been published in three papers (Nilssen et al. Hum. Mol. Genet. 6, 717-726. 1997; Liao et al. J. Biol. Chem. 271, 28348-28358. 1996; Nebes et al. Biochem. Biophys. Res. Commun. 200, 239-245. 1994). Curiously, the three sequences are not identical. When compared to the sequence of Nilssen et al. (accession # U60266.1) a TA to AT change at positions 1670 and 1671 resulting in a valine to asparitic acid substitution was found by Liao et al. and Nebes et al. Also a C to A change in pos 1152 was found which do not result in any changes in the amino acid sequence.

Diagnosis

The diagnosis of alpha-mannosidosis is currently is based on clinical evaluation, detection of mannose-rich oligosaccharides in urine, and direct measurements of alpha-mannosidase activity in various cell types, such as leukocytes, fibroblasts, and amniocytes (Chester et al., In: Durand P, O'Brian J (eds) Genetic errors of glycoprotein metabolism. Edi-Ermes, Milan, pp 89-120. 1982; Thomas and Beaudet. In: Scriver C R, Beaudet A L, Sly W A, Valle D (eds). The metabolic and molecular bases of inherited disease. Vol 5. McGraw-Hill, New York, pp 2529-2562. 1995).

Because the symptoms initially often are mild and the biochemical diagnosis is difficult, the diagnosis is frequently made late in the course of the disease. It is obvious that patients and their families would benefit substantially from an early diagnosis.

Animal Models

Alpha mannosidosis has been described in cattle (Hocking et al. Biochem J 128:69-78. 1972), cats (Walkley et al. Proc. Nat. Acad. Sci. 91: 2970-2974, 1994), and guinea pigs (Crawley et al. Pediatr Res 46: 501-509, 1999). A mouse model was recently generated by targeted disruption of the alpha-mannosidase gene (Stinchi et al. Hum Mol Genet 8: 1366-72, 1999). Like in humans alpha mannosidase seems to be caused by specific mutations in the gene coding for lysosomal alpha-mannosidase. Berg et al. (Biochem J. 328: 863-870.1997) reported the purification of feline liver lysosomal alpha-mannosidase and determination of its cDNA sequence. The active enzyme consists of 3 polypeptides, with molecular masses reported to be 72, 41, and 12 kD. Similarly to the human enzyme it was demonstrated that the feline enzyme is synthesized as a single-chain precursor with a putative signal peptide of 50 amino acids followed by a polypeptide chain of 957 amino acids, which is cleaved into the 3 polypeptides of the mature enzyme. The deduced amino acid sequence was 81.1% and 83.2% identical with the human and bovine sequences, respectively. A 4-bp deletion was identified in an affected Persian cat; the deletion resulted in a frameshift from codon 583 and premature termination at codon 645. No enzyme activity could be detected in the liver of the cat. A domestic long-haired cat expressing a milder phenotype had enzyme activity of 2% of normal; this cat did not possess the 4-bp deletion. Tollersrud et al. (Eur J Biochem 246:410-419. 1997) purified the bovine kidney enzyme to homogeneity and cloned the gene. The gene was organized in 24 exons that spanned 16 kb. Based on the gene sequence they identified two mutations in cattle.

Medical Need for Alpha-Mannosidosis Therapy

In light of the severe clinical manifestations resulting from the accumulation of mannose-rich oligosaccharides, the lack of effective treatment for alpha-mannosidosis is well recognised. At present, the major therapeutic option for treatment of the disease is bone marrow transplantation, however, it is the aim of the present invention to promote enzyme replacement therapy as a potential future alternative.

Bone Marrow Transplantation

In 1996 Walkley et al. (Proc. Nat. Acad. Sci. 91: 2970-2974, 1994) published a paper on three kittens with mannosisdosis that were treated with bone marrow transplantation (BMT) in 1991. In the 2 animals that were sacrificed a normalisation was seen, not only in the body, but more importantly, also in brain. The third cat was well after 6 years. Normally, an untreated cat dies with 3-6 months. In 1987 a child with mannosidosis was treated with BMT (Will et al. Arch Dis Child 1987 October; 62(10):1044-9). He died after 18 weeks due to procedure related complications. In brain little enzyme activity was found. This disappointing result could be explained by heavy immunosuppressive treatment before death, or that it takes time for the enzyme activity to increase in brain after BMT. The donor was the mother (who as carrier must be expected to have less than 50% enzyme activity) or it may be BMT in man has no effect on enzyme function in brain. Despite having variable outcomes the few attempts of bone marrow transplantation have thus indicated that successful engraftment can correct the clinical manifestations of alpha-mannosidosis, at least in part. However, the challenge of reducing the serious procedure related complications when applying bone marrow transplantation in human therapy still remains to be defeated.

Enzyme Replacement Therapy

When lysosomal storage diseases were discovered, hopes were raised that this could be treated by enzyme substitution. Enzyme replacement therapy has proven efficient in Gaucher disease. When exogenous lysosomal glucocerebrosidase is injected into the patient, this enzyme is taken up by enzyme-deficient cells (Barton et al. N Engl J Med 324: 1464-1470). Such uptake is regulated by certain receptors on the cell surface as for instance the mannose-6-phosphate receptor, which is nearly ubiquitous on the surface of cells and other receptors such as the asialoglycoprotein receptor and the mannose receptor, which are restricted to certain cell types such as cells of the monocyte/macrophage cell line and hepatocytes. The cellular uptake of the enzyme is therefore heavily dependent upon its glycosylation profile. If properly designed, the deficient enzyme could be replaced by regular injections of exogenous enzyme in the same manner as diabetic patients receive insulin. In vitro studies with the purified active lysosomal alpha-mannosidase added to the media of enzyme-deficient fibroblasts showed correction of the lysosomal substrate accumulation. In vivo treatment, on the other hand, has been hampered in part by the problem of producing the sufficient quantity of enzymes, due to difficult large scale production and purification procedures, and by complications resulting from immune reactions against the exogenous enzyme. Most importantly, however, special considerations apply in relation to lysosomal storage diseases with a major neurological component, such as alpha-mannosidosis, wherein the clinical manifestations are related to increased lysosomal storage within the central nervous system. Thus, enzyme replacement therapy has not proven effective against the acute neuronopathic variant of Gaucher disease (Prows et al. Am J Med Genet 71:16-21). The delivery of therapeutic enzymes to the brain is prevented by the absence of transport of these large molecules through the blood-brain barrier. From the general notion that the blood brain barrier must be circumvented in order to see an effect of therapeutic agents in the brain, the use of a large diversity of delivery systems have been contemplated. These include invasive techniques such as osmotic opening of the blood brain barrier with for instance mannitol and non-invasive techniques such as receptor mediated endocytosis of chimeric enzymes. As enzyme replacement is expected to require administration of the enzyme on a regular basis, the use of invasive techniques should be avoided. Use of the non-invasive techniques, has only recently provided promising results in animal models (for alpha-mannosidosis see below, for other lysosomal disorders see for example: Grubb et al. PNAS 2008, 105(7) pp. 2616-2621). It has been contemplated that reduced storage in visceral organs and in the meninges could reduce the amount of oligosaccharides that is carried to the brain. Such considerations, however, are not considered to be applicable to lysosomal disorders in which the neurological damage is primary and severe (Neufeld, E. F. Enzyme replacement therapy, in "Lysosomal disorders of the brain" (Platt, F. M. Walkley, S. V: eds Oxford University Press).

However, as described in Roces et al. Human Molecular Genetics 2004, 13(18) pp. 1979-1988, Blanz et al. Human Molecular Genetics 2008, 17(22) pp. 3437-3445 and WO 05/094874 it has proven possible to increase levels of LAMAN in the central nervous system of animals using e.g. intravenous injection of a formulation comprising alpha-mannosidase thereby reducing intracellular levels of neutral mannose-rich oligosaccharides within one or more regions of the central nervous system. This indicates that recombinant alpha-mannosidase is useful in enzyme replacement therapy of patients suffering from alpha-mannosidosis. Thus, one major remaining hurdle towards providing efficient treatment of alpha-mannosidosis using enzyme replacement is providing sufficient amounts of pure recombinant alpha-mannosidase in a cost-efficient manner.

Production and Purification of Alpha-Mannosidase

WO 02/099092 discloses a small scale production process for rhLAMAN in CHO cells using serum free medium at 37° C. A small scale purification process is also described involving diafiltration of the crude enzyme and weak anion exchange chromatography using DEAE sepharose FF columns in the capture step, followed by a number of chromatographic purification steps involving hydrophobic interaction- and mixed mode chromatography.

WO 05/094874 discloses a small scale production process for rhLAMAN in Chinese Hamster Ovary (CHO) cells using serum free medium at 37° C. A small scale purification process analogous to the one of WO 02/099092 is also described. WO 05/077093 describes the manufacture of highly phosphorylated lysozymal enzymes. In example IV a purification method for acid alpha-glucosidase (GAA) using a multi-modal resin (blue-sepharose) is described. GAA, although a lysozymal enzyme, is however entirely different from rhLAMAN. GAA is highly phosphorylated, while rhLAMAN has a low degree of phosphorylation. Furthermore, the sequence identity score is less than 12% between GAA and rhLAMAN, and finally their theoretical isoelectric points differ by more than one pH unit (5.42 and 6.48 respectively). Thus the method as described in WO 05/077093 to purify GAA is not applicable to rhLAMAN. A small scale production process for rhLAMAN in CHO cells using 0.25% (V/V) serum and DMSO addition has been disclosed (Berg et al. Molecular Genetics and Metabolism, 73, pp 18-29, 2001. It also describes two purification processes involving a) a three-step procedure involving ultra-filtration, anion exchange chromatography and gel filtration or b) single-step immuno-affinity chromatography. It is further disclosed how method a) results in the 130 kDa enzyme fragmenting entirely into 55 kDa and 72 kDa fragments, whereas method b) results in partial fragmentation of the 130 kDa precursor into significant amounts of the 55 and 72 kDa fragments.

Hence, an improved process for production and purification of recombinant alpha-mannosidase would be advantageous. In particular, an improved process for large scale cultivation of a cell line capable of expressing alpha-mannosidase and a more efficient large scale purification process for isolating pure alpha-mannosidase with a high enzymatic activity from a cell culture would be advantageous.

SUMMARY OF THE INVENTION

Thus, an object of the present invention relates to a production and purification process for recombinant alpha-mannosidase.

In particular, it is an object of the present invention to provide a scalable production and purification process that solves the above mentioned problems of the prior art with providing sufficient amounts of high purity alpha-mannosidase with high enzymatic activity thereby providing a treatment for patients suffering from alpha-mannosidosis. Thus, one aspect of the invention relates to a process for purification of recombinant alpha-mannosidase from a cell culture, wherein a fraction of said cell culture comprising recombinant alpha-mannosidase is subjected to chromatography on a resin comprising a multi-modal ligand. The inventors surprisingly found that this purification process resulted in composition comprising recombinant alpha-mannosidase with higher purity and a higher percentage of the desired 130 kDa glycoprotein species than previously achieved. Achieving persistent high percentages (such as more than 80%) of the non-fragmented 130 kDa glycoprotein after purification is advantageous as this provides for a more uniform product as compared to a fragmented enzyme, which in turn enhances the ability to obtain a pharmaceutical grade product.

Another aspect of the present invention relates to a process for fed batch or continuous production of recombinant alpha-mannosidase, comprising the following steps:

a. inoculating a production reactor comprising a base medium with cells capable of producing recombinant alpha-mannosidase on day 0, to provide a cell culture;

b. adding a feed medium to said cell culture at least once from day 1;

c. adjusting the temperature of said cell culture to at the most 35° C., such as 34° C., 33° C., 32° C., preferably at the most 31° C., either after day 3 or when the viable cell density is higher than 2.1 MVC/mL, whichever comes first.

The inventors surprisingly found that the above production process resulted in a cell culture comprising recombinant alpha-mannosidase in high yields which was readily transferable to the purification column of the present invention without any dilution.

Yet another aspect of the present invention is to provide a composition comprising purified recombinant alpha-mannosidase, wherein at least 80% of the alpha-mannosidase is present as a 130 kDa glycoprotein.

One other aspect of the present invention is a composition comprising purified recombinant alpha-mannosidase for use in the treatment of alpha-mannosidosis.

Yet another aspect of the present invention is a method of treating alpha-mannosidosis and/or reducing or alleviating the symptoms associated with alpha-mannosidosis, said method comprising a step of administering a composition comprising purified recombinant alpha-mannosidase to a subject in need thereof.

Figure 1:
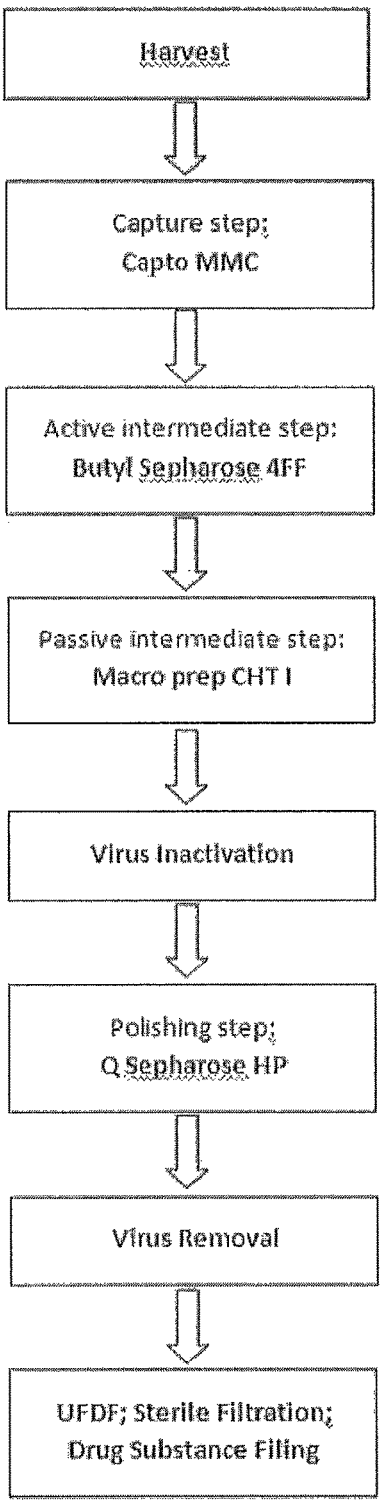
FIG. 1 shows an outline of the currently preferred purification process design for alpha-mannosidase from harvest to drug substance filing.

The present invention will now be described in more detail in the following.

DETAILED DESCRIPTION OF THE PREFERRED EMBODIMENT

Definitions

Prior to discussing the present invention in further details, the following terms and conventions will first be defined:

Recombinant Alpha-Mannosidase

In the context of the present invention recombinant alpha-mannosidase is defined as alpha-mannosidase which by virtue of its origin or manipulation is not equal to all or a portion of the wild-type alpha-mannosidases found in nature. Thus, it is constructed using recombinant techniques which involves recombinant DNA molecules, that is hybrid DNA sequences comprising at least two fused DNA sequences, the first sequence not normally being fused with the second sequence in nature. The recombinant alpha-mannosidase protein may be of human or non-human origin. In particular, it may be a recombinant human lysosomal alpha-mannosidase (rhLAMAN). The alpha-mannosidase product may be a single polypeptide or a mixture of a single polypeptide and fractions thereof. Also the alpha-mannosidase may be subject to posttranslational modifications and may therefore be in the form of a glycoprotein.

Cell Culture

A cell culture is the process by which cells are grown under controlled conditions. In the present context the cells of the cell culture are specifically designed to express a protein of interest, such as recombinant alpha-mannosidase. The cell culture may reside in a bioreactor, which is specially designed so as to allow control of the chemical and physical conditions.

Fraction

In the present context a fraction refers to a fraction of a cell culture. The fraction may constitute the whole cell culture, but is often a treated fraction of the culture, such as a clarified, filtered, concentrated, diluted or partly purified fraction.

Resin

In the context of the present invention a resin constitutes the basis of a stationary phase in a chromatography system, on which various chemical groups or substances are attached to provide a certain amount of affinity for a given molecule or protein of interest. Resins are often polymeric beads with ligands covalently attached, said resins being insoluble in the liquid mobile phases used.

Multi-Modal Ligand

By multi-modal ligand is meant any ligand which is designed to interact with a molecule or protein of interest in at least 2 ways. The individual interactions may independently be hydrophobic, hydrophilic, ionic, Van der Waals interactions, hydrogen bonding or any other intermolecular chemical or physical interaction. In the present context a ligand is an organic chemical substance attached to a resin as defined above. A multi-modal ligand will have different affinities for different substances that are passed through the chromatography column dissolved in a mobile phase. The differences in affinity leads to variations in retention time of the different substances on the chromatography column, enabling separation of the substances. The retention times are also dependent on other factors such as for example the constituents of the mobile phase, pH and temperature. Resins comprising multimodal ligands are sometimes referred to as "mixed mode" resins as well, but in the present context resins comprising a multi-modal ligand are not to be confused with so-called "mixed-mode ion exchange resins" which comprise several different "ligands" on the same resin which may have opposite charges, such as e.g. —OH, —Ca$^+$ and —PO$_4^{2-}$ in the case of ceramic hydroxyapatite resin (CHT). In these resins the individual ligands are not multi-modal.

Loading

In the present context loading refers to the transfer of a harvest, eluate or other solution onto a chromatographic system, such as a chromatography column comprising a resin as a stationary phase.

Buffer

The term buffer is well known as a general description of a solution containing either a weak acid and/or its corresponding salt or a weak base and/or its corresponding salt, which is resistant to changes in pH. In the context of the present invention the buffers used are suitable for use in chromatographic systems, such buffers include but are not limited to: Phosphate buffers, e.g. disodium phosphate (Na$_2$HPO$_4$), sodium phosphate or potassium phosphate, acetate buffers, e.g. sodium acetate or potassium acetate, sulphate buffers, e.g. sodium sulphate or potassium sulphate, ammonium sulphate or Hepes, or other buffers, e.g. sodium borate or tris-HCl buffer.

Ultrafiltration

Ultrafiltration is a separation method in which hydraulic pressure is used to force molecules and solvent across a membrane comprising pores of a particular size, also known as the cut-off size or value. Only molecules which have a molecular weight smaller than the cut-off value of the membrane are able to cross the membrane while those with a larger molecular weight do not cross the membrane and form the so called retentate. The molecules present in the retentate may thereby be concentrated as the solvent flows across the membrane.

In a particular embodiment the concentration of a solution or composition comprising a polypeptide such alpha-mannosidase may be performed by Tangential flow filtration (TFF). This method is in particular useful for large-scale concentration, i.e. for concentration of solutions with a volume from one liter to several hundreds of liters. Thus this method is in particular useful for production of concentrated solutions of a polypeptide of interests on an industrial scale. The TFF technique is based on the use of a particular apparatus which causes the solution which is to be filtrated to flow across a semi-permeable membrane; only molecules which are smaller than the membrane pores will pass through the membrane, forming the filtrate, leaving larger matter to be collected (retentate). With the TFF method two different pressures are applied; one to pump the solution into the system and to circulate it in the system (inlet pressure), and another pressure is applied over the membrane (membrane pressure) to force the small molecules and the solvent across the membrane. The inlet pressure may typically be in the range of 1-3 bar, such as between 1.5-2 bar. The transmembrane pressure (TMP) may typically be larger than 1 bar. The concentrated composition of a polypeptide of interest may be collected as the retentate when TFF is used to concentrate the composition. Membranes useful for TFF may typically be made of regenerated cellulose or polyethersulphone (PES).

Diafiltration

In the present context diafiltration is a filtration process where a species of interest is in the retentate, i.e. it is not allowed to pass through the filter, whereas other components such as for example buffers and salts do pass through the filter. Thus diafiltration may for example be used to exchange one buffer by another or to concentrate solutions containing a species of interest such as recombinant alpha-mannosidase. A first aspect of the present invention is to provide a process for purification of recombinant alpha-mannosidase from a cell culture, wherein a fraction of said cell culture comprising recombinant alpha-mannosidase is subjected to chromatography on a resin comprising a multi-modal ligand. The advantage of using resins comprising a multimodal ligand in the present context is that these resins enable binding of the alpha-mannosidase species in solutions having high conductivity levels. This has the advantage that undiluted harvest with high conductivity levels can be used, and no exchange of the harvest buffer is necessary. The chromatography step comprising a multi-modal ligand may therefore preferably be the first chromatography step after isolating the fraction from the cell culture. Said chromatography step comprising a multi-modal ligand may often be referred to as a "capture step", since the protein of interest is initially withheld on the column (i.e. captured), while many impurities pass through the column during washing steps. The protein is subsequently eluted using a specific elution buffer.

Thus, in one embodiment of the invention a process is provided wherein the fraction of the cell culture comprising the recombinant alpha-mannosidase is a clarified undiluted harvest. In the context of the present invention the term "clarified undiluted harvest" means a harvest of a cell culture, that is free of non-dissolved material or solids, i.e. it is a clear solution. The harvest may have been submitted to a treatment in order to convert it to a clear solution. Such treatments may include but are not limited to: Filtration and centrifugation. Furthermore, the harvest is not significantly diluted prior to subjection to chromatography steps. Hence the harvest is diluted by less than 10%, such as less than 7%, less than 5%, less than 2%, less than 1%, less than 0.5%, such as less than 0.1%. In the most preferred embodiment the harvest is not diluted.

In another embodiment a process is provided wherein the clarified undiluted harvest has a conductivity of 10-20 mS/cm, such as 12-17 mS/cm, preferably 15 mS/cm. The conductivity is measured prior to loading the harvest onto a chromatography system. In one embodiment said chromatography is performed on a resin comprising a multimodal ligand having a carboxylic acid or sulphonic acid group. The carboxylic and/or sulphonic acids comprised in these ligands may be in the protonated form or in a deprotonated (salt) form depending on the conditions in the chromatographic system, particularly the pH of the mobile phase.

In yet another embodiment a process is provided wherein the resin bound multi-modal ligand is a substance of formula (I), (II) or (III):

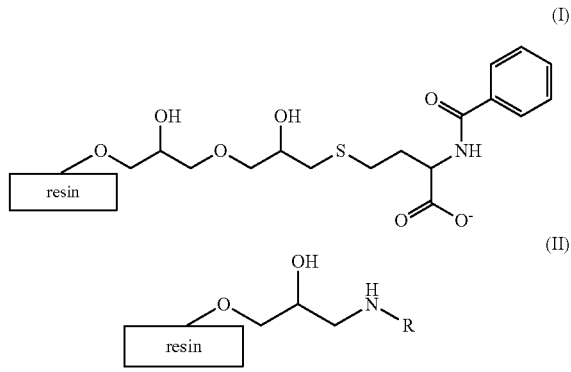

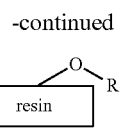

wherein R of the substances of formula (II) and (III) is a functional group of formula (IV):

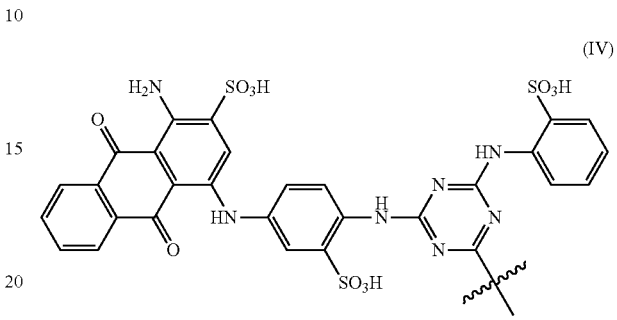

The multimodal ligand represented by the functional group of formula (IV) is generally referred to as "Cibracon Blue 3G" and examples of commercial products represented by the substances of formula (I), (II) and (III) are "Capto™ MMC", "Capto™ Blue" and "Blue Sepharose™ fast flow" respectively. Other useful resins of the multimodal type include: Capto™ Adhere, MEP HyperCel™, HEA HyperCel™ and PPA HyperCel™. In the context of the present invention such resins have been proven especially effective in the initial purification of an undiluted harvest comprising recombinant alpha-mannosidase.

An additional embodiment of the invention provides a process wherein the fraction of said cell culture loaded onto the resin comprising a multimodal ligand, is subjected to at least one washing step with a solution comprising isopropanol, preferably at least 1% (V:V) isopropanol, such as at least 2%, 3%, 4%, 4.5% (V:V) isopropanol, preferably at least 5% (V:V) isopropanol. The advantage of using a solution comprising isopropanol is that it provides for a better removal of unwanted host cell proteins (HCP's), specifically it helps to remove a protease responsible for the proteolytic degradation of the desired 130 kDa rhLAMAN species. HCP's are to understood as proteins endogenous to the host cell used in the cell culture during production. Although isopropanol is preferred other useful alcohols for this process includes ethanol, n-propanol and n-butanol.

In yet another embodiment a process is provided wherein the pH of the solution used for the washing step is in the range of pH 3.5-6.5, such as pH 4.0-6.0, pH 4.5-5.5, preferably pH 4.7-5.0. Another embodiment provides a process wherein the solution used for the washing step comprises an acetate buffer, preferably in a concentration in the range of 0.05-1.6M, such as 0.1-1.5M, 0.5-1.4M, 0.7-1.3M, 0.8-1.2M, 0.9-1.1M, preferably 0.95M. The acetate buffer may preferably be selected from the group consisting of sodium acetate, potassium acetate, lithium acetate, ammonium acetate.

Yet another embodiment provides a process wherein a first eluate comprising recombinant alpha-mannosidase is eluted from the resin comprising a multi-modal ligand using an aqueous solution comprising ethylene glycol or propylene glycol. The addition of ethylene glycol to the elution buffer was found to significantly enhance the yield of eluted recombinant alpha-mannosidase. Propylene glycol was also enhanced yield but ethylene glycol is preferred.

One embodiment provides a process wherein the concentration of ethylene glycol or propylene glycol in the aqueous solution is 20-60%, 20-50%, 25-50%, 30-50%, 35-45%, such as 40%.

In a preferred embodiment a process is provided wherein the aqueous solution comprising ethylene glycol or propylene glycol comprises sodium chloride. The addition of sodium chloride to this solution was found to significantly enhance yields by promoting the elution of the rhLAMAN enzyme.

In another embodiment the concentration of sodium chloride in the aqueous solution comprising ethylene glycol or propylene glycol is in the range of 0.2 to 2.4M, such as in the range of 0.4 to 2.2M, 0.6 to 2.0M, 0.8 to 1.9M, 1.0 to 1.8M, 1.2 to 1.7M, 1.4 to 1.6M, preferably 1.5M. Alternatively the concentration of sodium chloride maybe in the range of 0.2 to 1.6M or in the range of 1.4 to 2.4M.

In a preferred embodiment the aqueous solution comprising ethylene glycol or propylene glycol comprises a buffer. Said buffer may preferably be a phosphate buffer, such as sodium phosphate or potassium phosphate. Although phosphate buffers are preferred, additional useful buffers for the aqueous solution include citrate and borate buffers, Tris, MES, MOPS and Hepes buffers.

In another preferred embodiment the concentration of the buffering salts in the aqueous solution comprising ethylene glycol or propylene glycol is 50-350 mM, 55-300 mM, 65-280 mM, 70-250 mM, 75-200, 80-200 mM, 85-150 mM, preferably 90 mM.

In yet another preferred embodiment the pH of the aqueous solution comprising ethylene glycol or propylene glycol is pH 7.0-9.0, such as pH 7.1-8.5, pH 7.2-8.3, pH 7.5-8.0, preferably pH 7.7.

In one embodiment a process is provided wherein a first eluate comprising alpha mannosidase obtained from the resin comprising a multi-modal ligand is further subjected to a process comprising the steps of i) applying a fraction comprising alpha-mannosidase to a hydrophobic interaction chromatography resin to provide an eluate comprising the recombinant alpha-mannosidase, ii) passing a fraction comprising alpha-mannosidase through a mixed-mode ion exchange resin to allow retention of contaminates to provide a flow through comprising the recombinant alpha-mannosidase, and iii) subjecting a fraction comprising alpha-mannosidase to chromatography on a anion exchange resin to provide a eluate comprising the recombinant alpha-mannosidase.

In one embodiment a process is provided involving steps i)-iii) as described above, wherein the fraction in step i) has been subject to a purification on said resin comprising a multimodal ligand, the fraction of step ii) is derived from the eluate from step i) and the fraction of step iii) is derived from the flow through from step ii). In other words steps i) to iii) are performed in the order they are listed, however without precluding intermediate steps in between steps i) to iii). These may be intermediate purification steps and/or virus reduction or virus removal steps. In a preferred embodiment the hydrophobic interaction chromatography resin of step i) is an alkyl substituted resin, preferably butyl sepharose resin. Alkyl substituted resins may include ethyl-, butyl- and octyl sepharose resins. Furthermore, phenyl sepharose resins are also applicable. Examples of such resins are Butyl-S Sepharose™ 6 Fast Flow, Butyl Sepharose™ 4 Fast Flow, Octyl Sepharose™ 4 Fast Flow, Phenyl Sepharose™ 6 Fast Flow (high sub) and Phenyl Sepharose™ 6 Fast Flow (low sub), Butyl Sepharose™ High Performance, Phenyl Sepharose™ High Performance. The advantage of a purification step involving hydrophobically interacting resins and particularly butyl sepharose resin is effective removal of host cell proteins and DNA residues, while retaining good yield of the rhLAMAN enzyme.

In yet another embodiment step i) comprises at least one washing step, wherein the solution used for washing comprises a phosphate buffer and an acetate buffer, preferably sodium phosphate and sodium acetate. This dual buffer washing step has proved especially effective in removing impurities such as host cell proteins and DNA residues.

In yet another embodiment the concentration of phosphate buffer in the dual buffer washing of step i) is in the range of 5-40 mM, such as 10-30 mM, 15-25 mM, preferably 20 mM, and the concentration of acetate buffer is in the range of 0.9-1.5M, such as 1.0-1.4M, 1.1-1.3M, preferably 1.2M.

In another embodiment step i) comprises at least one washing step, wherein the solution used for washing comprises no more than one buffer, preferably a phosphate buffer, preferably sodium phosphate.

In another embodiment the one buffer of the at least one washing step comprising no more than one buffer is present in a concentration in the range of 0.4-0.8M, such as 0.5-0.7M, preferably 0.6M.

In one embodiment a process is provided wherein the mixed-mode ion exchange resin of step ii) is a ceramic hydroxyapatite or fluoroapatite resin, preferably ceramic hydroxyapatite type I (CHT I) resin. Applying this chromatography step has been shown to efficiently separate a significant amount of DNA impurities from the recombinant alpha-mannosidase composition and bind host cell proteins while the rhLAMAN enzyme product passes the column without binding.

In another embodiment the anion exchange resin of step iii) is a strong anion exchange resin, such as a quaternary ammonium strong anion exchange resin. Such resins are included but not restricted to the following examples: Q-Sepharose™ HP Q-Sepharose™ FF, DEAE-Sepharose™, Capto™ Q, Uno™ Q, ANX Sepharose™.

In yet another embodiment a process is provided wherein a virus inactivation step is performed, preferably in between step ii) and step iii). In a preferred embodiment the virus inactivation step comprises mixing the flow through of step ii) with an aqueous solution of isopropanol (1:1 V/V of flow through/aqueous isopropanol) for at least 2 hours, preferably followed by concentration by ultrafiltration and removal of isopropanol using diafiltration. The aqueous isopropanol during inactivation may be in the range of 10-50% isopropanol, such as 20-40%, 25-35%, 28-32%, preferably 30% isopropanol. The 1:1 V/V solution of flow through and aqueous isopropanol thus has a final concentration of isopropanol of 15%.

Another preferred embodiment is a process wherein a virus reduction step is performed, preferably after chromatography step iii).

In one embodiment the virus reduction step comprises filtration of a solution comprising recombinant alpha-mannosidase, preferably the eluate of step iii), through a filter, preferably a virus removal filter, such as a Ultipor™ VF grade DV20 filter, or a Planova™ 15N or 20N filter, Preferably a Planova™ 15N filter is used.

The purification process of the present invention may advantageously be performed on a large scale, thus in preferred embodiments the process is performed on chromatography columns having a column volume of at least 0.5 L, such as at least 1.0 L, 2.0 L, 5.0 L, 10 L, preferably at least 13.0 L.

In another embodiment of the present invention a purification process as described above is provided, wherein the alpha-mannosidase has a sequence selected from:
A) the sequence set forth in SEQ ID NO 2
B) an analogue of the sequence in A
C) a subsequence of the sequence in A) or B)

Where the sequence described by SEQ ID NO 2 represents the amino acid sequence for the recombinant human lysosomal alpha-mannosidase (rhLAMAN) as provided in WO 02/099092.

By "subsequence" is meant a fragment of the parent sequence having a size of no less than 50% of the parent sequence, such as no less than 55%, 60%, 65%, 70%, 75%, 80%, 85%, 90% or no less 95% of the parent sequence. Accordingly, the subsequences in question may have a length of from 505-1009 consecutive amino acid residues, such as from 525-1009, from 550-1009, 575-1009, 600-1009, 625-1009, 650-1009, 675-1009, 700-1009, 725-1009, 750-1009, 775-1009, 800-1009, 825-1009, 850-1009, 875-1009, 900-1009, 925-1009, 950-1009, 975-1009, 980-1009, 990-1009 or such as from 1000-1009 consecutive amino acid residues. Furthermore, the relevant subsequences of SEQ ID NO: 2 or analogues thereof must retain the catalytic site. Although the 3D structure of human LAMAN is unknown, the 3D structure of the bovine LAMAN has been reported and based on that data it has been concluded that the following amino acids participate in the active site and/or are responsible for coordinating the $Zn^{2+}$ atom required for activity also in human LAMAN: AA 72=H, AA 74=D, AA 196=D, AA 446=H (UniProtKB/Swiss-Prot database: 000754, MA2B1_HUMAN_, Heikinheimo et al. J. Mol. Biol. 327, 631-644, 2003). It has been shown that mutations of AA 72 and 196 in human LAMAN results in almost complete loss of enzyme activity (Hansen et al., Biochem. J. (2004), 381, pp. 537-567). In order to display activity, a subsequence of the rhLAMAN should retain at least the regions containing the above four amino acids. Preferably, the subsequences of rhLAMAN also comprise one or more additional conformational parts, including for example binding sites, beta-turns, disulfide bridges, stop codons and others. In the human form of LAMAN there are several disease causing mutations indicating importance for that particular amino acid, e.g. AA 53, 72, 77, 188, 200, 355, 356, 359, 402, 453, 461, 518, 563, 639, 714, 750, 760, 801, 809, 916 (The human gene mutation database, HMDG® professional, Cardiff University, 2009) and there are also amino acids which are of importance for glycosylations, including AA 133, 310, 367, 497, 645, 651, 692, 766, 832, 930 and 989 and amino acids involved in disulfide bridges such as AA 55+358, 268+273, 412+472 and 493+501.

By "analogue" is meant a sequence with a certain percentage of sequence identity with the parent sequence, this may be at least 60% sequence identity, such as at least 70%, 80%, 85%, 90%, 95%, 98% or preferably 99% sequence identity It will be understood that the analogues and subsequences set forth above are preferably functionally equivalent to the alpha-mannosidase having the amino acid sequence set forth in SEQ ID NO: 2 in the sense that they are capable of exerting substantially the same enzymatic activity.

The term "substantially the same enzymatic activity" refers to an equivalent part or analogue having at least 50%, preferably at least 60%, more preferably at least 70%, more preferably at least 75%, more preferably at least 80%, more preferably at least 85%, more preferably at least 90%, more preferably at least 95% and most preferably at least 97%, at least 98% or at least 99% of the activity of the natural enzyme. An example of a functionally equivalent analogue of the enzyme could be a fusion protein which includes the catalytic site of the enzyme in a functional form, but it can also be a homologous variant of the enzyme derived from another species. Also, completely synthetic molecules that mimic the specific enzymatic activity of the relevant enzyme would constitute "functionally equivalent analogues". Non-human analogues of LAMAN are generally not applicable for therapy as they can potentially induce the formation of antibodies in the patient and cause disease. Human analogues however may be useful in enzyme replacement therapy, when the mutations are not disease causing and do not diminish the desired enzyme activity significantly. Examples of such mutations are: His70Leu, Gln240Arg, Ser250Ala, Leu278Val, Ser282Pro, Thr312Ile, Ala337Arg, Ser413Asn, Ser481Ala, Gln582Glu, Arg741Gly, Thr873Pro (Source: www.ensembl.org.; transcript ID ENST00000456935). Also Pro669Leu and Asp402Lys are known by the inventors not to cause disease. Generally, the skilled person will be able to readily devise appropriate assays for the determination of enzymatic activity. For LAMAN, an appropriate enzyme activity assay is disclosed in WO 02/099092 page 26, lines 8-28. Briefly, the following procedure may be performed for screening purposes using flat-bottomed 96-well plates: 75 µl of 4× assay buffer (8 mM p-Nitrophenyl-alpha-D-mannopyranoside, 2 mg/mL BSA, 0.4M Na Acetate (pH 4.5) is added to 75 µl of sample or an appropriate dilution of it (in 10 mM Tris pH 7.4 containing 150 mM NaCl+10% superblock). The plates are incubated at 37 deg C. for 30 min and stopped with 75 µl of 1.8M $Na_2CO_3$ and the absorbance recorded at 405 nm on a plate reader. The 96-well plates are read on a spectrophotometer. Specific activity is defined as µmoles of p-Nitrophenyl-alpha-D-mannopyranoside hydrolysed per minute per mg protein.

As commonly defined "identity" is here defined as sequence identity between genes or proteins at the nucleotide or amino acid level, respectively. Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length. One may manually align the sequences and count the number of identical amino acids. Alternatively, alignment of two sequences for the determination of percent identity may be accomplished using a mathematical algorithm. Such an algorithm is incorporated into the NBLAST and XBLAST programs. BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search, which detects distant relationships between molecules. When utilising the NBLAST, XBLAST, and Gapped BLAST programs, the default parameters of the respective programs may be used. See www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

Another embodiment of the present invention is a composition comprising alpha-mannosidase obtainable by the purification process described above. In a second aspect of the present invention a process is provided for fed batch or continuous production of recombinant alpha-mannosidase, comprising the following steps: a. inoculating a production reactor comprising a base medium with cells capable of producing recombinant alpha-mannosidase on day 0, to provide a cell culture; b. adding a feed medium to said cell culture at least once from day 1; c. adjusting the temperature of said cell culture to at the most 35° C., such as 34° C., 33° C., 32° C., preferably at the most 31° C., either after day 3 or when the viable cell density is higher than 2.1 MVC/mL, whichever comes first.

In the above process inoculation day is defined as day 0, and the following day is day 1 and so on. The starting temperature used from day 0 until the adjustment described in point c. is in the range 36-37° C., preferably 36.5° C. It is to be understood that the abovementioned temperatures are actual measured temperatures, not set points, i.e. in the bioreactor setup used for the present invention the temperature of 31° C. mentioned above required a temperature set point of 32° C. Likewise a temperature of 36.5° C. requires a set point temperature of 37° C.

Suitable host cells for the expression and production of recombinant alpha-mannosidase are derived from multicellular organisms, preferably from mammals.

In particular, the cells used to produce recombinant alpha-mannosidase may be selected from the group consisting of monkey kidney CVI line transformed by SV40 (COS-7); human embryonic kidney line (293 or 293 cells subcloned for growth in suspension culture); baby hamster kidney cells (BHK); Chinese hamster ovary cells/-DHFR (CHO); mouse Sertoli cells (TM4); monkey kidney cells (CV I); African green monkey kidney cells (VERO-76); human cervical carcinoma cells (HELA); canine kidney cells (MDCK); buffalo rat liver cells (BRL 3A); human lung cells (W138); human liver cells (Hep G2, HB 8065); mouse mammary tumor (MMT 060562); TM cells; MRC 5 cells; FS4 cells; and a human hepatoma line (Hep G2). Insect cell lines or human fibroblast cells are also available as suitable host cells. Production of recombinant alpha-mannosidase is obtained using cells transfected with an appropriate nucleic acid construct using techniques known to the skilled person. In particular, the nucleic acid construct may comprise a nucleic acid sequence selected from the group consisting of: i) the nucleic acid sequence set forth in SEQ ID NO: 1; and ii) a nucleic acid sequence coding for a sub-sequence or analogue of the sequence set forth in SEQ ID NO 2 as provided above.

The cells may preferably be a rLAMAN Chinese Hamster Ovary (CHO) cell line developed specifically for the purpose of producing recombinant enzyme as described in WO 02/099092. A culture of this cell line DSM ACC2549 which was deposited at the DSMZ GmbH, Maschroderweg 1b, D-38124 Braunschweig, Germany for the purpose of patent deposit according to the Budapest treaty on 6 Jun. 2002. This cell may be obtained using the expression plasmid pLaman-Expi having the sequence shown in SEQ ID NO 1.

The process of steps a-c may further comprise the following step: d. A process for purification of recombinant alpha-mannosidase from said cell culture, wherein a fraction of said cell culture comprising recombinant alpha-mannosidase is subjected to chromatography on a resin comprising a multi-modal ligand having a carboxylic acid or sulphonic acid group, as described above.

In yet another embodiment the cell culture used in the production process is essentially free of any supplements derived from animals, such as cod liver oil supplements. Avoiding the use of such supplements reduces the risk of viral contamination in the final enzyme product.

In one preferred embodiment of the production process the undiluted harvest of the fed batch or continuous production has a concentration of alpha-mannosidase of at least 0.1 g/L, such as at least 0.2 g/L, 0.3 g/L, 0.4 g/L, preferably at least 0.5 g/L.

In another embodiment the undiluted harvest of the fed batch or continuous production has an enzyme activity in the range of 3-35 U/mL, such as 5-35 U/mL, 7-35 U/mL, preferably in the range of 10-35 U/mL. It is to be understood that upon further process optimization the enzyme activity of the harvest may become even higher than 35 U/mL.

The production process may advantageously be performed at a large scale. Thus in one embodiment the process for fed batch or continuous production is performed at a volume of at least 30 L, such as at least 50 L, 75 L, 100 L, 150 L, 200 L, preferably at least 250 L.

In another embodiment of the present invention a production process as described above is provided, wherein the alpha-mannosidase has a sequence selected from:
  A) the sequence set forth in SEQ ID NO 2
  B) an analogue of the sequence in A
  C) a subsequence of the sequence in A) or B)

Another embodiment of the present invention is a composition comprising alpha-mannosidase obtainable by the production process described above. Such compositions may in preferred embodiments comprise additional active product ingredients (API), adjuvants, and/or excipients.

In a third aspect of the present invention a composition is provided comprising purified recombinant alpha-mannosidase, wherein at least 80% of the alpha-mannosidase is present as a 130 kDa glycoprotein.

In a preferred embodiment the composition comprising purified recombinant alpha-mannosidase is provided wherein the recombinant alpha-mannosidase remains stable in liquid solution for at least 4 days when stored at +5° C. or for at least 24 months when stored at −20° C.

The currently preferred composition for the formulation buffer solution for the rhLAMAN enzyme product is described below and the achieved stabilities are also listed:
Na$_2$HPO$_4$ 3.50 mM (Dibasic sodium phosphate)
NaH$_2$PO$_4$ 0.17 mM (Monobasic sodium phosphate)
Glycine 27 mM
Mannitol 250 mM
pH 7.70, 290 mOsm/kg (isotonic solution)

| In-use stability: | Stable solution | +5° C.-4 days |
| --- | --- | --- |
| | | +20° C.-6 hours |
| | | −20° C.-24 months |
| | Freeze Dried | +5° C.-24 months |

In another embodiment of the present invention a composition as described above is provided, wherein the alpha-mannosidase has a sequence selected from:
A) the sequence set forth in SEQ ID NO 2
B) an analogue of the sequence in A
C) a subsequence of the sequence in A) or B)

Another preferred embodiment is the above composition comprising purified recombinant alpha-mannosidase for use as a medicament.

In a further embodiment the above composition comprising purified recombinant alpha-mannosidase is for use in the treatment of alpha-mannosidosis.

Yet another embodiment is the use of the above composition comprising purified recombinant alpha-mannosidase for the preparation of medicament for the treatment of alpha-mannosidosis. Another embodiment is a method of treating alpha-mannosidosis and/or reducing or alleviating the symptoms associated with alpha-mannosidosis, said method comprising a step of administering a composition comprising a purified recombinant alpha-mannosidase as provided above to a subject in need thereof.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Abbreviations Used

CIP: Clean In Place
CV: Column Volume
Cv: viable cell density
DF: Diafiltration
DO: Dissolved Oxygen
IPA: Isopropanol
MVC/mL: 10$^6$ viable cells/mL
NaPi: Sodium Phosphate
NaAc: Sodium Acetate
OD: Optical Density
EG: ethylene Glycol
TFF: Tangential Flow Filtration
TMP: Transmembrane pressure
UF: Ultrafiltration Example 1—Currently Preferred Overall Purification Procedure The purification procedure for obtaining the optimum yields and purities for alpha-mannosidase in the context of the present invention is as described below. Standard conditions for regeneration and cleaning of resins are used, as prescribed for the individual resin (see also examples 2-5). The resins used are available at GE healthcare life sciences and BioRad.

Providing fraction of a harvest from a production of alpha-mannosidase, and clarifying the fraction without significant dilution. Preferably no dilution at all is made.

Performing a capture step involving column chromatography of the above fraction on a resin comprising a multimodal ligand. These resins are selected from the group consisting of: Capto™ MMC, Capto™ Adhere, PlasmidSelect™ Xtra, Capto™ Blue, Blue Sepharose™ Fast Flow resin, MEP HyperCel™, HEA HyperCel™ and PPA HyperCel™.

Several washes are performed at pH 4.5-8.5, and the wash buffers are selected from the group consisting of: sodium acetate, potassium acetate, ammonium acetate, sodium phosphate, potassium phosphate, sodium sulphate, potassium sulphate, ammonium sulphate, MES, MOPS, Hepes, sodium borate, tris-HCl, citrate buffer or combinations thereof (buffer group A, hereinafter). In at least one wash however, the washing solution comprises isopropanol and the pH is between pH 4-6. The elution buffer is selected from buffer group A, and the elution solution comprises ethylene glycol. Elution pH is kept at pH 7.0-8.5.

Performing an active intermediate step involving column chromatography of a composition comprising alpha-mannosidase on a hydrophobic interaction resin. These resins are selected from the group consisting of: Butyl-S Sepharose™ 6 Fast Flow, Butyl Sepharose™ 4 Fast Flow, Octyl Sepharose™ 4 Fast Flow, Phenyl Sepharose™ 6 Fast Flow (high sub) and Phenyl Sepharose™ 6 Fast Flow (low sub), Butyl Sepharose™ High Performance, Phenyl Sepharose™ High Performance.

Several washes are performed at pH 7-8. The wash buffers are selected from buffer group A. The elution buffer is also selected from buffer group A and elution pH is between pH 7-8.

Performing a passive intermediate step involving column chromatography of a composition comprising alpha-mannosidase on a mixed-mode ion exchange resin to provide a flow-through. These resins are selected from the group consisting of: ceramic hydroxyapatite type I or II (preferably type I) resin, or fluoroapatite. One wash is performed to provide a flow-through at pH 7-8. The wash buffer is selected from buffer group A.

Performing a polishing step involving column chromatography of a composition comprising alpha-mannosidase on an anion exchange resin. These resins are selected from the group consisting of: Q-Sepharose™ HP, Q-Sepharose™ FF, DEAE-Sepharose™, Capto™ Q, Uno™ Q, ANX Sepharose™.

Several washes are performed at pH 7-8. The wash buffers are selected from buffer group A and TRIS-HCl buffer. The elution buffer is also selected from buffer group A and elution pH is kept between pH 7-8.

Performing a virus inactivation step by bringing a solution of the alpha-mannosidase in contact with isopropanol.

Performing a virus removal step using nano-filtration.

The yields and product components ratios for the purified composition comprising alpha-mannosidase according to the present invention are shown in the below table 1, with comparison to previous methods, wherein:

Method 1 is: The currently preferred method according to the present invention.

Method 2 is: Similar to method 1 without a polishing step. It is also without washing steps comprising isopropanol for the capture step and with fewer washes in the active intermediate step, and finally it is without virus inactivation/removal steps.

Method 3 is: As described in WO 02/099092 (multimodal ligands not used).

TABLE 1 yields and purities resulting from past and current purification procedures

| Method | Overall yield | Overall purity | %130 kDa | %55 kDa | %75 kDa | Scale (Culture volume) |
|---|---|---|---|---|---|---|
| 1 | 70% | 99.6% | 95.2% | 1.5% | 2.9% | 250 L |
| 2 | 60-70% | 98.2% | 92.1% | 2.6% | 3.5% | 30 L |
| 3 | 70-80% | 80% | <80% | >5% | >5% | 1 L |

Figure 7A:
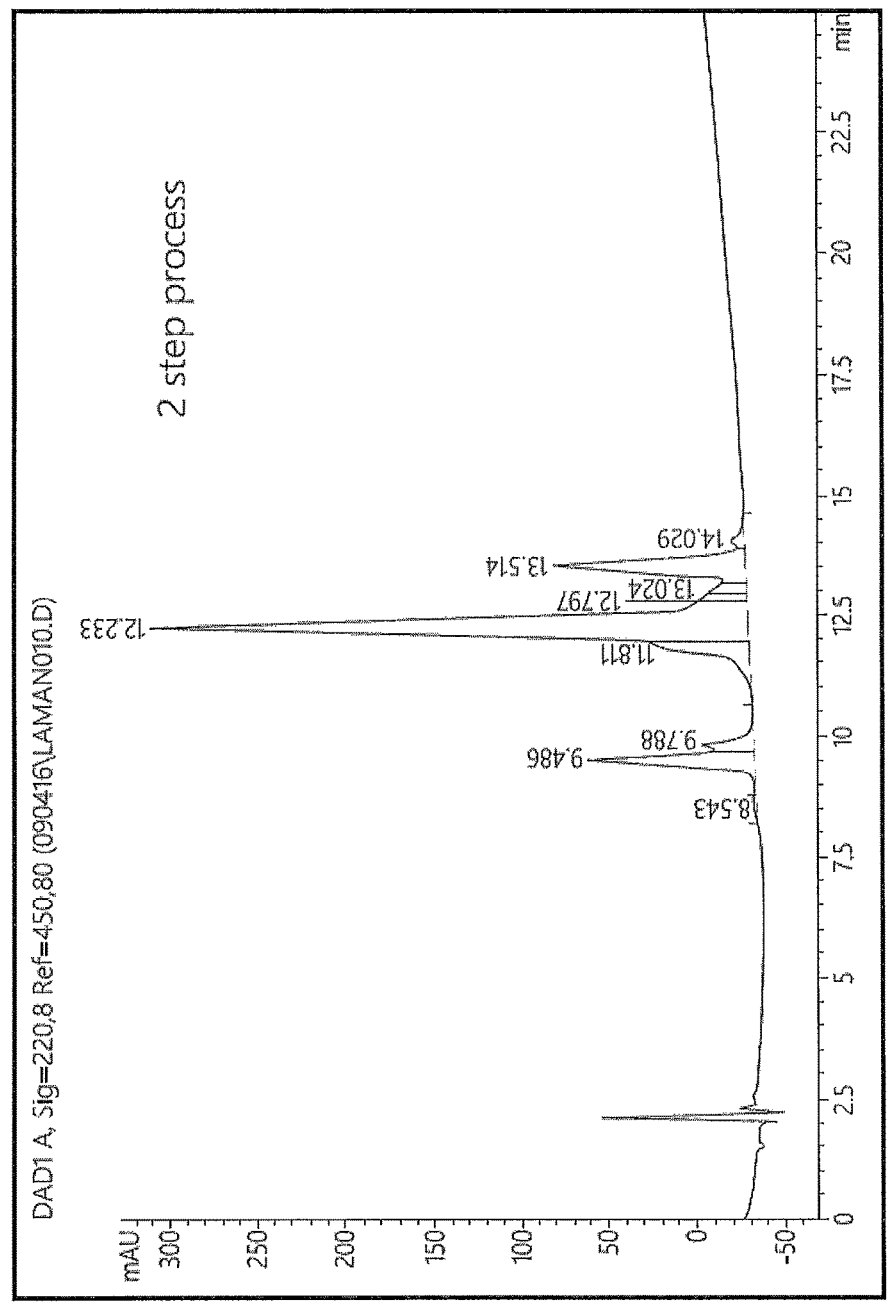
FIG. 7A shows an HPLC diagram for purified alpha-mannosidase using a 2 step process where the amount of 130 kDa species is depicted as compared to the 55 and 75 kDa species. The first peak from the left is the 55 kDa species, followed by the 130 kDa and 75 kDa species respectively. The 2 step process is without the use of a multimodal ligand chromatography step.
Figure 7B:
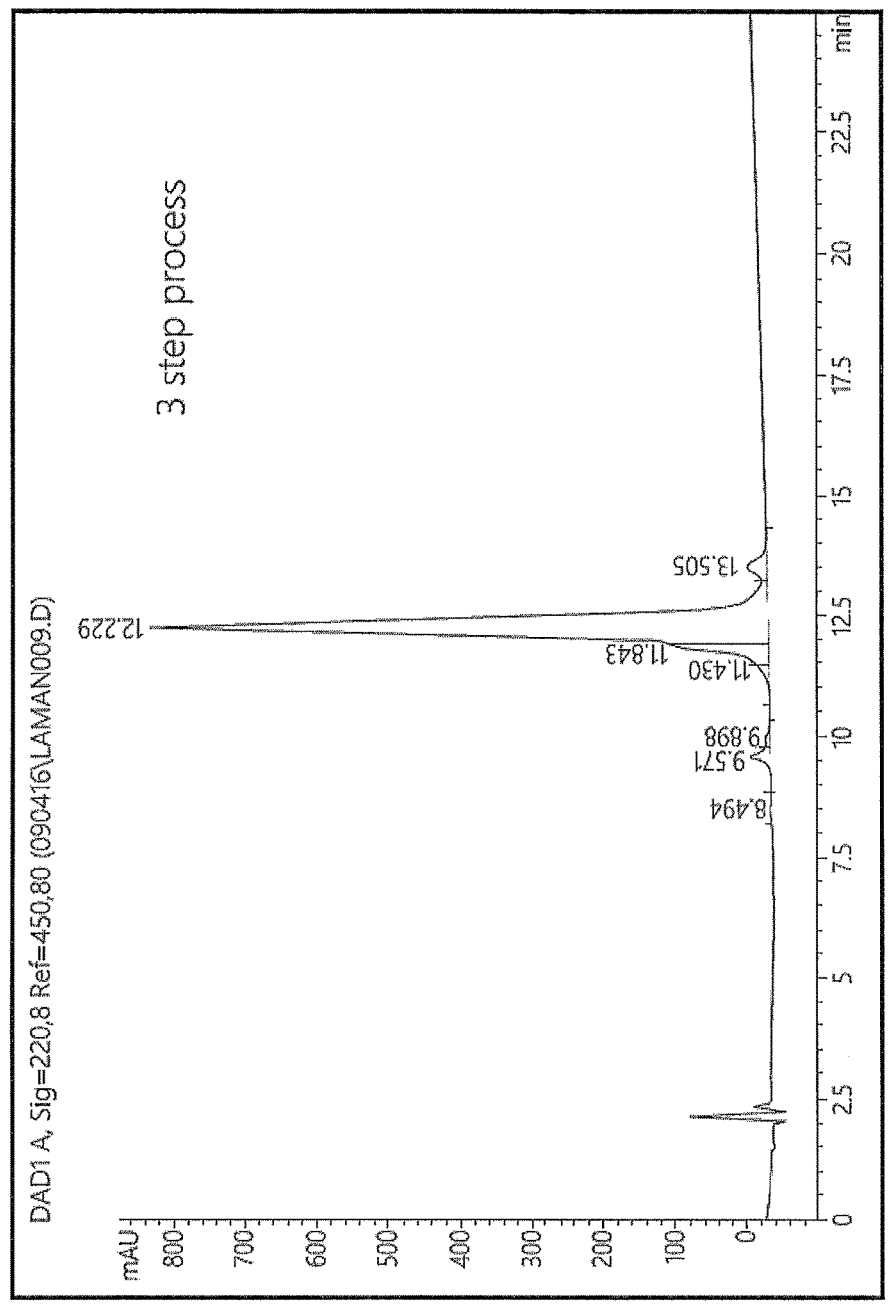
FIG. 7B shows an HPLC diagram for purified alpha-mannosidase using a 3 step process where the amount of 130 kDa species is depicted as compared to the 55 and 75 kDa species. The first peak from the left is the 55 kDa species, followed by the 130 kDa and 75 kDa species respectively. The 3 step process uses a multimodal ligand chromatography step.
Figure 7C:
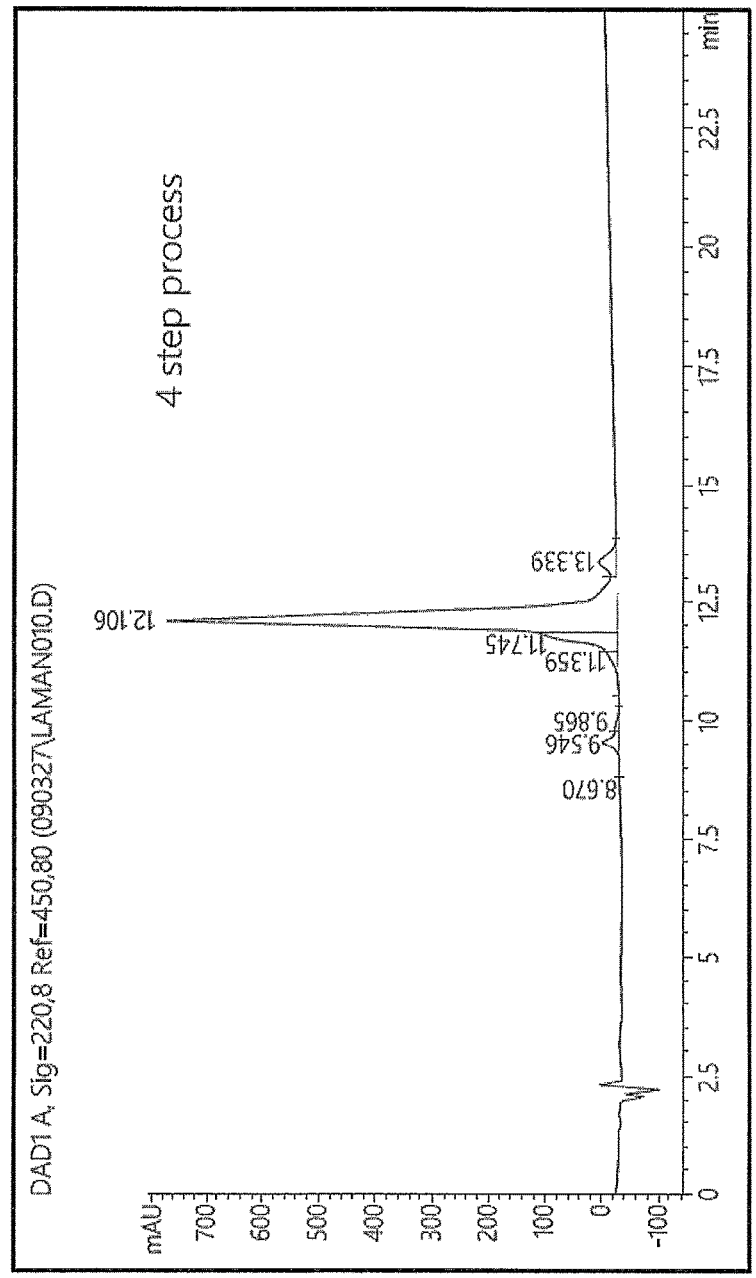
FIG. 7C shows an HPLC diagram for purified alpha-mannosidase using a 4 step process where the amount of 130 kDa species is depicted as compared to the 55 and 75 kDa species. The first peak from the left is the 55 kDa species, followed by the 130 kDa and 75 kDa species respectively. The 4 step process uses a multimodal ligand chromatography step.

See also example 10 and FIG. 7.

Example 2—Chromatographic Capture Step Using a Multi Modal Ligand

Clarified undiluted harvest comprising alpha-mannosidase binds by mixed mode interaction to a multimodal ligand type resin such as Capto™ MMC as used in this example. Increasing salt and addition of ethylene glycol elutes the product. The capacity of Capto™ MMC was 260 U/ml resin. The capture stage was performed using the following steps:

Regenerate the column with 1-2 column volumes (CV) of 3M NaCl, pH 10-12 at 300 cm/hr.

Equilibrate with 5 CV of 50 mM sodium phosphate buffer (NaPi), 0.15M NaCl pH 7.5 at 300 cm/hr.

Load clarified, undiluted harvest (conductivity ~15 mS/cm) at 300 cm/hr.

Wash 1: 4 CV of equilibration buffer.

Wash 2: 3 CV of 0.95M NaAc, 5% (v:v) isopropanol, pH 4.9 at 300 cm/hr.

Wash 3: 4 CV of equilibration buffer (until stable baseline, ~0.06 Au with 5 mm flowcell) of equilibration buffer at 300 cm/hr.

Elute the product with 6 CV of 1.5M NaCl, 40% ethylene glycol in 90 mM NaPi, pH 7.7 at maximum 120 cm/hr. Start collecting when the absorbance increases (around 10 mAu from the new baseline). Collect ~4 CV.

Regenerate the column, as above with 3 CV, downward flow direction, maximum 120 cm/hr.

Clean in place (CIP) and sanitize, preferably with upward flow direction, with 3 CV $H_2O$, 3 CV 1M NaOH (~60 minutes contact time), 2-3 CV of phosphate buffer, pH ~7, 3 CV 20 mM sodium phosphate+20% ethanol. Store in 20 mM sodium phosphate+20% ethanol.

Figure 2:
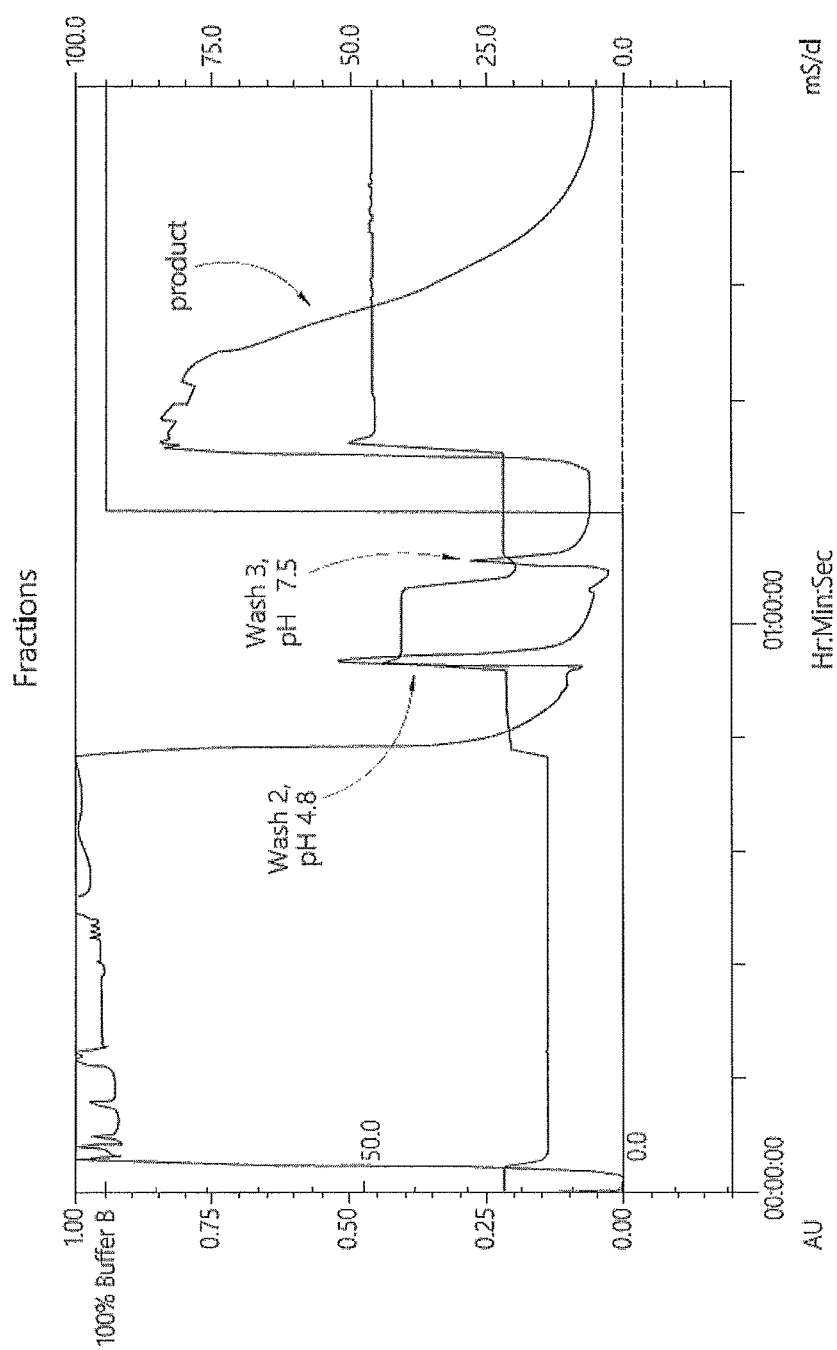
FIG. 2 shows an example of a Capto™ MMC column chromatogram for alpha-mannosidase.

Table 2 shows an example of a purification scheme. Table 3 summarizes the step. FIG. 2 shows an example of a chromatogram for this step.

TABLE 2

Capture stage purification scheme: Capto ™ MMC packed in a 13.5 × 2 ml (27 ml) XK 16 column

| Step | Vol. (ml) | Activity (U/ml) | Total activity (U) | OD 280 divided by 1.8 | Yield (%) | HCP µg/ml |
|---|---|---|---|---|---|---|
| Load | 439 | 15 | 6585 (=244 U/ml resin) | | | |
| Flow through + 1st equilibration (eq) buffer wash | 560 | | ~37 | | 0.6 | |
| 0.95M NaAc + 5% IPA, pH 4.9 | 90 | | 0 | | | |
| Eq. buffer | 101 | 0.3 | 30 | | 0.5 | |
| Eluate | 118 | 50 | 5900 | 2.2 | 89 | 28 |

TABLE 3

Summary of conditions for Capto ™ MMC capture stage

| Step | Buffer | Flow rate (cm/hr) | Volume (CV) | Flow Direction |
|---|---|---|---|---|
| Regeneration | 3M NaCl, pH ~11 | 300 | 2 | down |
| Equilibration | 50 mM NaPi, 150 mM NaCl, pH 7.5 | 300 | 5 | down |
| Load | Harvest | 300 | | down |
| Wash 1 | 50 mM NaPi, 150 mM NaCl, pH 7.5 | 300 | 4 | down |
| Wash 2 | 0.95M NaAc, 5% IPA, pH 4.8 | 300 | 3 | down |
| Wash 3 | 50 mM NaPi, 150 mM NaCl, pH 7.5 | 300 | 4 | down |
| Elution | 90 mM NaPi, 1.5M NaCl, 40% EG, pH 7.7 | ≤120 | 6 | down |
| Regeneration | 2M NaCl, pH ~11 | 120 | 3 | down |
| Flush | Water | 300 | 3 | up |
| CIP | 1M NaOH | 300 | 3 | up |
| Conditioning | Phosphate buffer (RB to decide) | 300 | 1-3 | up |
| Storage | 20 mM NaPi + 20% Ethanol | 100 | 3 | up |

Example 3—Chromatographic Intermediate Active Step Using Hydrophobic Interaction The product from the capture stage comprising alpha-mannosidase binds by hydrophobic interactions after addition of sodium sulfate to hydrophobic interaction type resins, such as Butyl Sepharose™ 4 FF as used in this example. Reducing the salt concentration elutes the product. The capacity was 195 U/ml resin. The following steps were used in the intermediate active stage:

Regenerate the column with 1 CV 20 mM sodium phosphate (NaPi) buffer, pH 7.5 at 100 cm/hr.

Equilibrate the column with 5 CV 0.5M $Na_2SO_4$, 20 mM NaPi, pH 7.5 at 150 cm/hr.

Mix the product pool from step 1 with the same volume 20 mM NaPi, 0.8M $Na_2SO_4$, pH 7.5 and load it onto the column at 70 cm/hr. The mixing can be performed in-line or maximum 3 hours before loading starts. The 1:1 volume:volume (v:v) mix corresponds to approximately 1.11:1, weight:weight (w:w) (eluate: sodium sulfate buffer). If needed the conditioned load should be filtered through 0.45 µm filter (hydrophilic PES or PVDF) before loading.

Wash the column with 3 CV of equilibration buffer at 70 cm/hr to remove ethylene glycol, in addition to host cell proteins, from the previous step.

Wash with 3.5 CV of 20 mM NaPi, 1.2M NaAc, pH 7.5 at 100 cm/hr.

Wash with 3.5 CV of 0.6M NaPi, pH 7.0 at 150 cm/hr.

Elute the product with 4 CV of 60 mM NaPi, pH 7.5 at 150 cm/hr. Collect the peak from the initial increase of absorbance until baseline is reached, ~2 CV.

Regenerate the column with 2 CV 20 mM NaPi, pH 7.5 followed by 3 CV $H_2O$ at 150 cm/hr.

Clean and sanitize with 3 CV 1M NaOH (60 min contact time), 1 CV $H_2O$, 1-3 CV of phosphate buffer and 2 CV 20 mM sodium phosphate+20% ethanol. Store in 20 mM sodium phosphate+20% ethanol.

Figure 3:
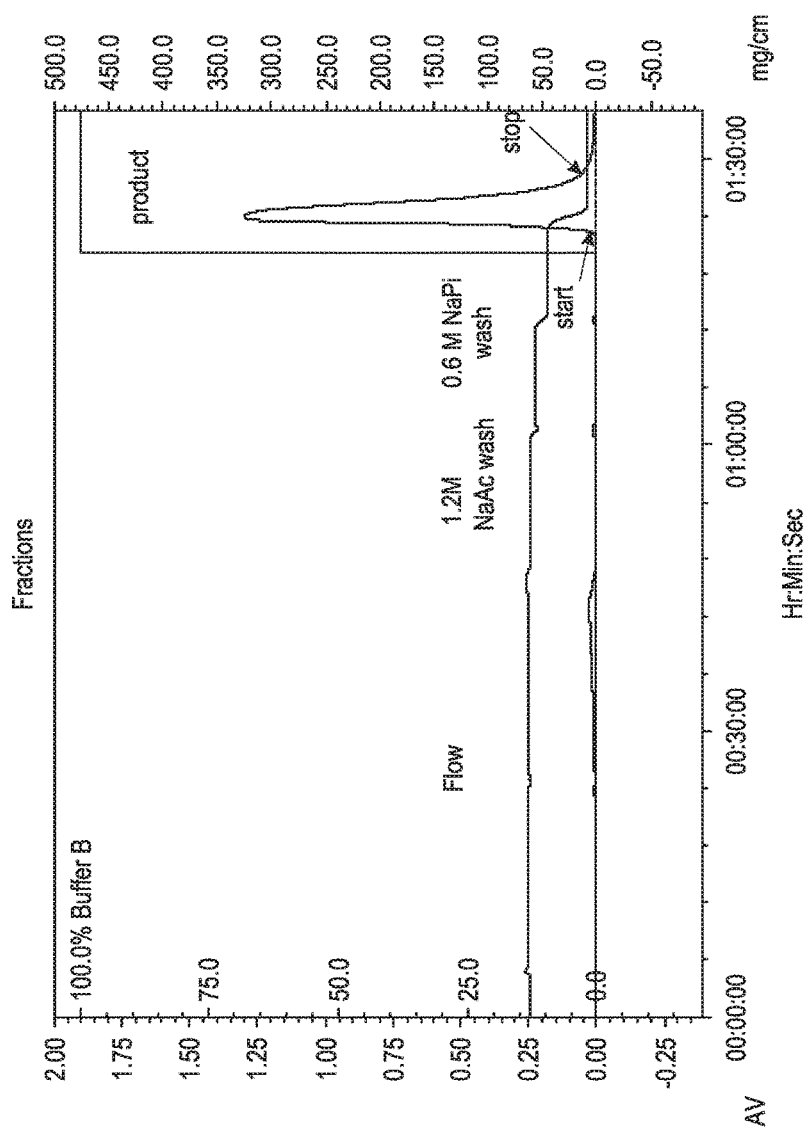
FIG. 3 shows an example of a butyl Sepharose™ FF column chromatogram for alpha-mannosidase.

Table 4 shows an example of a purification scheme. Table 5 summarizes the step. FIG. 3 shows an example of a chromatogram for this step.

TABLE 4

Intermediate active purification scheme using Butyl Sepharose ™ 4FF packed in a 13.5 cm H 2 cm² (27 ml) XK 16 column

| Step | Volume (ml) | Activity (U/ml) | Total activity (U) | OD 280 divided by 1.8 | Yield (%) | HCP ng/mg |
|---|---|---|---|---|---|---|
| Load | 236 | 23 | 5413 (=200 U/ml resin) | | | |
| Flow through + eq buffer wash | ~390 | 0.3 | ~100 | | 1.8 | |
| 1.2M NaAc, pH 7.5 | 95 | 0.5 | 48 | | 0.8 | |
| 0.6M NaPi, pH 7.0 | 97 | 0.2 | 19 | | 0.3 | |
| Eluate | 66 | 81 | 5346 | 3 | 98 | 940 |

TABLE 5

Summary of conditions for Butyl Sepharose ™ 4FF step

| Step | Buffer | Flow rate (cm/hr) | Volume (CV) | Flow Direction |
|---|---|---|---|---|
| Regeneration | 20 mM NaPi, pH 7.5 | 150 | 1 | down |
| Equilibration | 20 mM NaPi, 0.5M sodium sulfate, pH 7.5 | 150 | 5 | down |
| Load | Conditioned Capto MMC eluate | 70 | ~6 | down |
| Wash 1 | 20 mM NaPi, 0.5M sodium sulfate, pH 7.5 | 70 | 3 | down |
| Wash 2 | 20 mM NaPi, 1.2M NaAc, pH 7.5 | 100 | 3.5 | down |
| Wash 3 | 0.6M NaPi, pH 7.0 | 150 | 3.5 | down |
| Elution | 60 mM NaPi pH 7.5 | 150 | 4 | down |
| Regeneration | 20 mM NaPi, pH 7.5 | 150 | 2 | down |
| Flush | water | 150 | 3 | up |
| CIP | 1M NaOH | 150 | 3 | up |
| Flush | water | 150 | 1 | up |
| Conditioning | Phosphate buffer (RB to decide) | 150 | 1-3 | up |
| Storage | 20 mM Na-Pi + 20% Ethanol | 150 | 3 | up |

Example 4—Chromatographic Intermediate Passive Step Using Mixed-Mode Ion Exchange Two eluates comprising alpha-mannosidase from the intermediate active step were pooled and mixed 1:1 (weight: weight) with water to reduce the conductivity and loaded onto a mixed-mode ion exchange resin, such as in this example a Ceramic Hydroxyapatite I (CHT I) resin. The product passes without binding, while host cell proteins bind to the column. The flow through, containing the product was collected. The capacity was 550 U/ml resin. The following steps were used in this example of an intermediate passive stage:

Regenerate the column with 2 CV of 0.6M NaPi pH 7.0 at 300 cm/hr.

Equilibrate the column with 5 CV of 60 mM NaPi, pH 7.5 at 300 cm/hr.

Load the conditioned eluate from step 2 at 300 cm/hr and collect the flow through, containing the product. The conductivity and pH of the load will be ~10 mS/cm and 7.3, respectively. Collect the flow through, containing the product from an OD increase of 20 mAu until OD is back to 20 mAU, approximately the loading volume and 2 CVs wash. End-of step filter the product pool through 0.45 μm hydrophilic PES or PVDF filter.

Wash the column with 4 CV equilibration buffer at 300 cm/hr.

Regenerate the column with 3 CV of 0.6M NaPi, pH 7.0 at 300 cm/hr.

Clean and sanitize with 3 CV 1M NaOH (60 min contact time), 1 CV of 60 mM NaPi, pH 7.5 and 2 CV 20 mM sodium phosphate+20% ethanol. Store in 20 mM sodium phosphate+20% ethanol.

Figure 4:
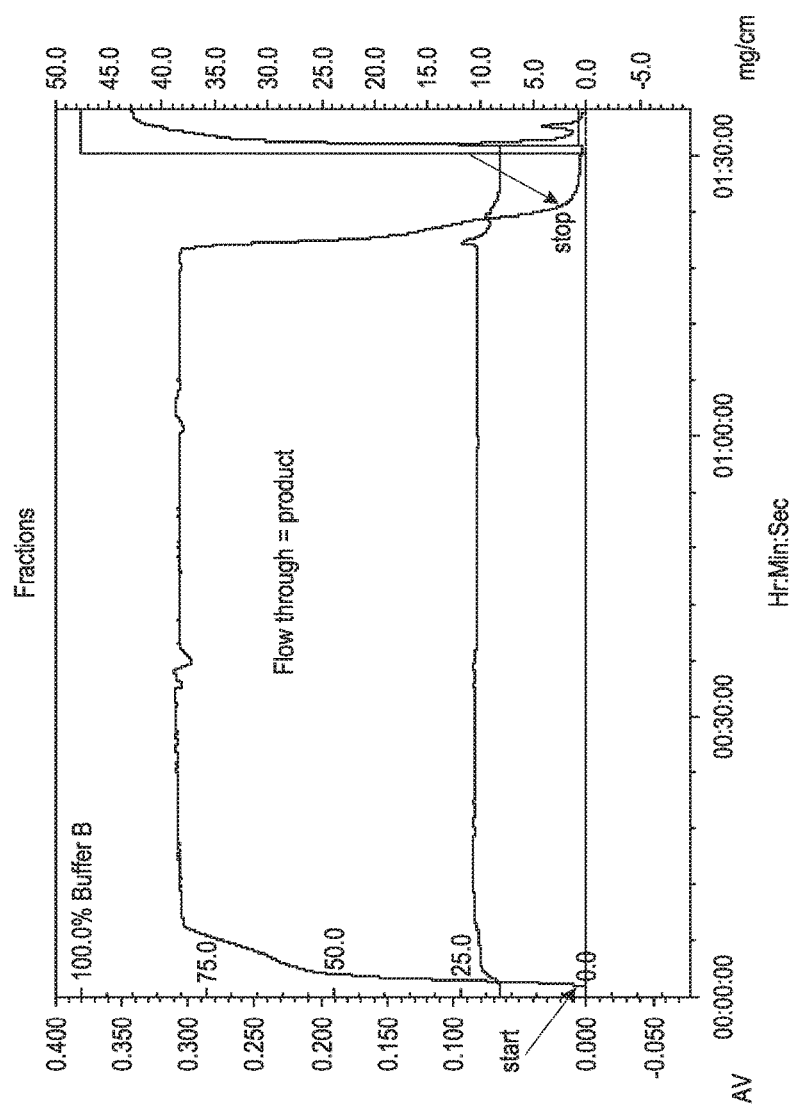
FIG. 4 shows an example of a CHT type 1 column chromatogram for alpha-mannosidase.

Table 6 shows an example of a purification scheme. Table 7 summarizes the step. FIG. 4 shows an example of a chromatogram for this step.

TABLE 6

Purification scheme for intermediate passive stage using CHT I packed in a 10 cm × 2 cm2 (20 ml) XK 16 column

| Step | Volume (ml) | Activity (U/ml) | Total activity (U) | OD 280 divided by 1.8 | Yield (%) | HCP ng/mg |
|---|---|---|---|---|---|---|
| Load | 360 | 31.6 | 11390 (=570 U/ml resin) | | | |
| Flow through = product end-of step filtered | 392 | 27.5 | 10780 | | 95 | ~500 |
| 0.5M NaPi | 40 | 0.45 | 18 | | | |

TABLE 7

Summary of conditions for CHT I step

| Step | Buffer | Flow rate (cm/hr) | Volume (CV) | Flow Direction |
|---|---|---|---|---|
| Regeneration | 600 mM NaPi, pH 7.0 | 300 | 2 | down |
| Equilibration | 60 mM NaPi, pH 7.5 | 300 | 5 | down |
| Load | Butyl eluate + $H_2O$ | 300 | | down |
| Wash 1 | 60 mM NaPi, pH 7.5 | 300 | 4 | down |
| Regeneration | 600 mM NaPi, pH 7.0 | 300 | 3 | down |
| CIP | 1M NaOH | ≤300 | 3 | up |
| Conditioning | NaPi buffer (RB to decide) | 300 | 1 | up |
| Storage | 20 mM NaPi + 20% Ethanol | 300 | 3 | up |

Example 5—Virus Inactivation Step

Virus inactivation may be performed at different stages of the process. In this example the virus inactivation was performed after the intermediate passive step and prior to the polishing step. Virus inactivation of the intermediate passive pool comprising alpha-mannosidase is obtained by 135±15 min incubation at 21±5° C. with 15% isopropanol (1:1 mixture with 30% aqueous isopropanol). The tank can be cooled by a cooling jacket at +4° C. to keep the process at 21±5° C. Tangential flow filtration (TFF), with 100 kDa polyethersulfone membrane, Screen A (from Millipore or Sartorius) was used to remove the isopropanol and change to sodium phosphate buffer. The following steps were used to inactivate viruses in this example:

Mix the product (flow through) from the intermediate passive step with 30% isopropanol in 60 mM sodium phosphate, 1:1 (v:v), which corresponds to 1:0.94 (w/w). Mix, e.g. by recirculation pumping. The product protein concentration will be ~0.3-1 mg/ml.

Incubate the solvent/product pool at room temperature for 135±15 min.

Equilibrate the TFF membrane with 60 mM sodium phosphate buffer.

Concentrate the pool to target concentration 2 mg/ml (0.5-3 mg/ml) by ultrafiltration at transmembrane pressure (TMP) 1.1 bar, at 21±5° C. pressure in =~1.4-1.5 bar and pressure out=0.7~-0.8 bar.

Exchange ~6 volumes by diafiltration against 60 mM sodium phosphate buffer. Start at TMP 1 bar (1.4 bar in/0.6 bar out). After the first volume is exchanged the TMP can be increased to 1.1.

Collect the retentate. Rinse the membrane with 2-3 system volumes of dilution buffer to remove loosely bound product. Collect the rinse together with the retentate. The final target protein concentration is 2 mg/ml (0.5-3 mg/ml).

Clean the membrane with $H_2O$, followed by 0.5M NaOH (60 min contact time). Store in 0.1M NaOH.

Table 8 shows the conditions for the virus inactivation/TFF step

TABLE 8

Summary of conditions for virus inactivation/TFF step

| Step | Buffer | Dil. w:w | UF | DF | TMP bar | Comment |
|---|---|---|---|---|---|---|
| Start | 30% IPA/ 70% NaPi | 1.94 x | | | | 135 ± 15 min, RT |
| Equilibration | NaPi | | | | | |
| UF | | | ~5x | | 1.1 (1.5in/ 0.7 out) | Concentrate to 2 mg/ml (0.5-3 mg/ml), flux ~100-65 LMH |
| DF | NaPi | | | 6x | 1.0-1.1 (1.5in/ 0.7 out) | First volume at lower TMP (1.4in/ 0.6out), then increase to TMP 1.1, flux ~65-100 LMN |
| System wash | NaPi | | | | | 2 system volumes, pool with retentate to target concentration 2 mg/ml (0.5-3 mg/ml) |
| Rinse | water | | | | | |
| CIP | 0.5-1M NaOH | | | | | |
| store | 0.1M NaOH | | | | | |

NaPi = 60 mM sodium phosphate, pH 7.5

Example 6—Chromatographic Polishing Step Using Anion Exchange

The conductivity of the retentate comprising alpha-mannosidase from the intermediate passive stage, was reduced by dilution 6 times with conditioning buffer (20 mM Tris-HCl, 10 mM NaCl, 75 mM mannitol, 0.005% Tween™ 80, pH 7.5) in order to bind by ionic interaction onto a anion exchange resin, such as in this example a quarternary ammonium high performance strong anion exchange resin (Q Sepahrose™ HP resin). The retentate was either diluted directly before loading or by in-line dilution. The product was eluted, into a container prefilled with 1CV of elution buffer, by addition of sodium chloride. The capacity is 400 U/ml resin. The following steps were used for the polishing stage in this example:

Regenerate the column with 1 CV 50 mM NaPi, 1M sodium chloride, pH 7.5 at 120 cm/hr.

Equilibrate the column with 5 CV 20 mM Tris-HCl, 10 mM sodium chloride, pH 7.5 at 120 cm/hr.

Load the diluted retentate from step 4 at 120 cm/hr.

Wash the column with 5 CV of equilibration buffer and 1 CV of 20 mM sodium phosphate, pH 7.5 at 120 cm/hr.

Elute the product with 4 CV of 50 mM sodium phosphate, 0.2M sodium chloride, pH 7.5 at 120 cm/hr into the prefilled (1 CV of elution buffer) container. Collect the peak from the initial increase (start collect at 10-20 mAu) of absorbance until 30-50 mAu (2 mm flowcell), 0.5-1.5 CV.

Regenerate the column with 3 CV 50 mM NaPi, 1M sodium chloride, pH 7.5 at 120 cm/hr.

Clean and sanitize with 3 CV 1M NaOH (60 min contact time) and 3 CV 10 mM NaOH. Store in 10 mM NaOH.

Figure 5:
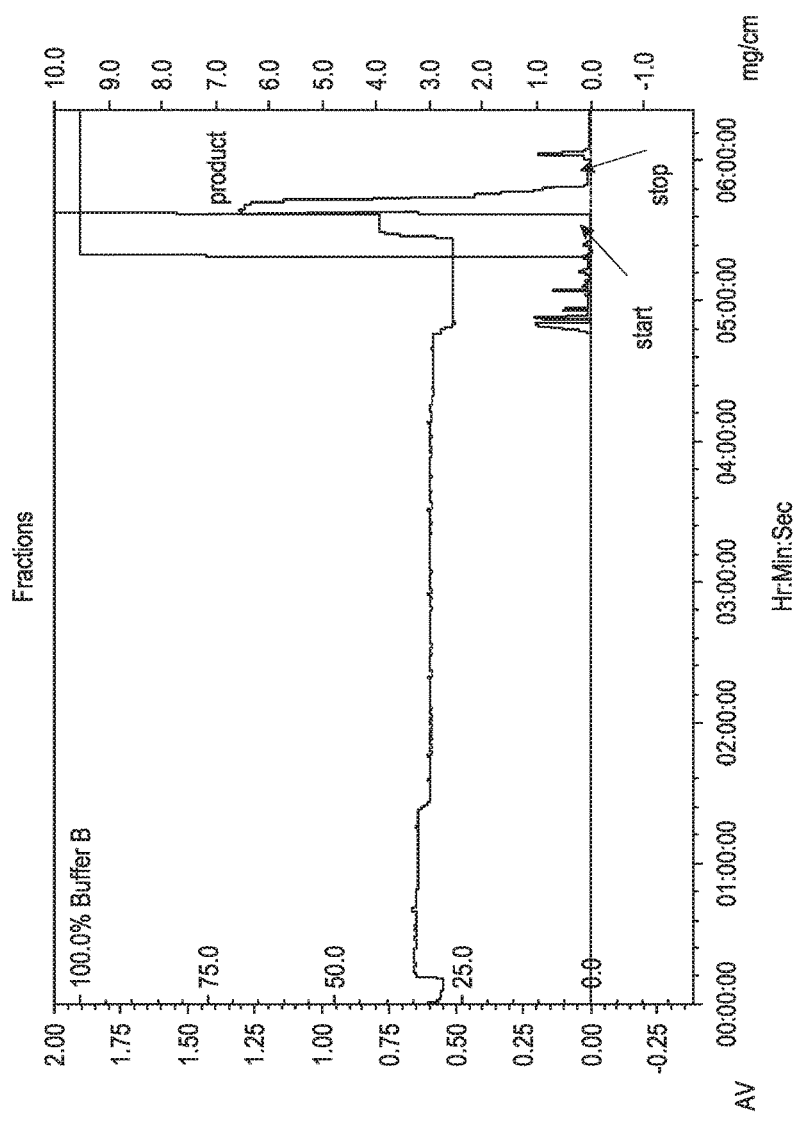
FIG. 5 shows an example of a Q Sepharose™ HP column chromatogram for alpha-mannosidase.
Figure 6:
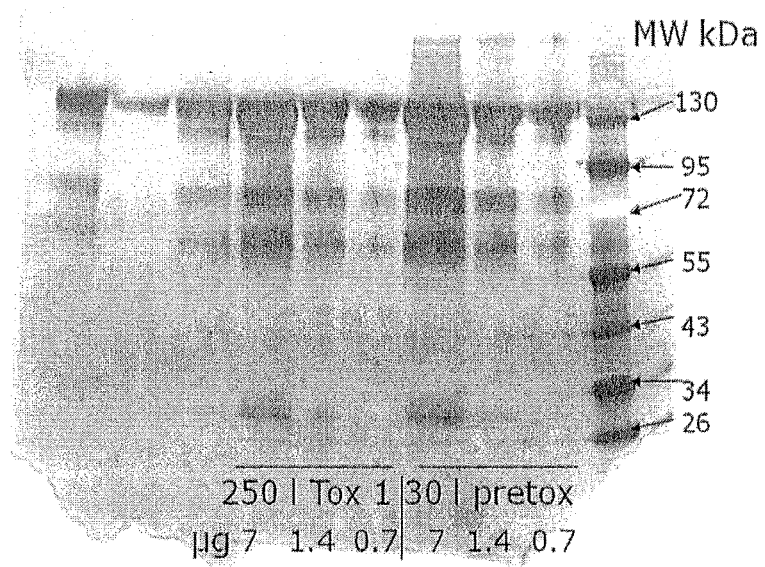
FIG. 6 shows an SDS-page chromatogram of the purified alpha-mannosidase composition indicating the distribution of the 130 kDa, 75 kDa and 55 kDa glycoprotein species.

Table 9 shows an example of a purification scheme. Table 10 summarizes the step. FIG. 5 shows an example of a chromatogram.

TABLE 9

Example of purification scheme for polishing step using Q Sepharose ™ HP resin 19 cm × 2 cm² (38 ml)

| Step | Volume (ml) | Activity (U/ml) | Total activity (U) | OD 280 divided by 1.8 | Yield (%) | HCP ng/mg |
|---|---|---|---|---|---|---|
| Load | 1095 | 9.6 | 10500 (=276 U/ml resin) | | | |
| Flow through | ~1300 | 0.07 | ~90 | | ~1 | |
| 20 mM sodium phosphate Wash | 75 | 1.7 | 127 | | ~1 | |
| Eluate | 69 (=49 ml eluate + 20 ml prefill) | 145 | 10024 | 5.3 | 95.5 | |

TABLE 10

Summary of conditions for Q Sepharose ™ HP step

| Step | Buffer | Flow rate (cm/hr) | Volume (CV) | Flow Direction |
|---|---|---|---|---|
| Regeneration | 50 mM NaPi, 1M NaCl pH 7.5 | 120 | 1 | down |
| Equilibration | 20 mM Tris-HCl, 10 mM NaCl pH 7.5 | 120 | 5 | down |

TABLE 10-continued

Summary of conditions for Q Sepharose ™ HP step

| Step | Buffer | Flow rate (cm/hr) | Volume (CV) | Flow Direction |
|---|---|---|---|---|
| Load | Conditioned retentate step 4 | 120 | | down |
| Wash | 20 mM Tris-HCl, 10 mM NaCl pH 7.5 | 120 | 5 | down |
| Wash | 20 mM NaPi, pH 7.5 | 120 | 1 | down |
| Elution into prefilled bag | 50 mM NaPi, 0.2M NaCl, pH 7.5 | 120 | 4 | down |
| Regeneration | 50 mM NaPi, 1M NaCl pH 7.5 | 120 | 3 | down |
| CIP | 1M NaOH | 120 | 3 | up |
| Storage | 10 mM NaOH | 300 | 3 | up |

Example 7—Virus Reduction Step

Virus reduction may be performed at different stages of the process. In this example the virus reduction was performed after the polishing step. The eluate from the polishing step is nanofiltered, after 0.1 μm pre-filtration, through a Planova™ 15N filter. The following steps were used:

The eluate from the polishing step is pre-filtered through a 0.1 μm filter. The filter is rinsed with a small volume of 50 mM sodium phosphate, 0.2M sodium chloride, pH 7.5 to remove loosely bound product.

The eluate is filtered at pressure 0.8 bar, at room temperature. The filtration is followed by a post wash of approximately three Planova 15 system volumes with 50 mM sodium phosphate, 0.2M sodium chloride, pH 7.5.

Example 8—Formulation and Storage

Tangential flow filtration (TFF), with a 100 kDa, Screen A, polyethersulfone membrane (Sartorius™ or Millipore™) changes the buffer to formulation buffer. The tank can be cooled by a cooling jacket at +4° C. to keep the process at 21±5° C. The estimated capacity is 100 l/m². The following steps were used for formulation and storage:

Equilibrate the membrane 3.5 mM $Na_2HPO_4$, 0.17 mM $NaHPO_4$, 250 mM mannitol, 27 mM glycine, pH 7.7 (formulation buffer).

Dilute the purified product comprising alpha-mannosidase with approximately 1 volume formulation buffer to target concentration 2-3 mg/ml. If the protein concentration is low in the product it is possible (but not necessary) to concentrate to 4-6 mg/ml to reduce the volume before dilution with formulation buffer.

Concentrate ~twice to target concentration 6 mg/ml by ultrafiltration at TMP 0.8 and at 21±5° C.

Exchange 6 volumes by diafiltration against formulation buffer at TMP 0.8, 21±5° C.

Concentrate ~1.5 times by ultrafiltration and collect retentate. Rinse the membrane with 1 system volume of formulation buffer to remove loosely bound product. Collect the rinse together with the retentate. An alternative is to measure OD 280 in the rinse and pool only if it contains product. The final target protein concentration is 7±2 mg/ml.

Clean the membrane with $H_2O$, followed by 0.5M NaOH (60 min contact time). Store in 0.1M NaOH.

TABLE 11

Summary of conditions for the formulation TFF step

| Step | Buffer | UF/DF dil. factor | Target conc. (mg/ml) | TMP (bar) | Comment |
|---|---|---|---|---|---|
| Dilution of step 6 product | Formulation buffer | 2 | 2-3 | | If protein conc. is <4 mg/ml in step 6 product a UF step can be introduced before dilution |
| Equilibration | Formulation buffer | | | | |
| UF | | 2 | 6 ± 2 | 0.8 | 1.1 bar in/0.5 bar out |
| DF | Formulation buffer | 6 ± 2 | 6 ± 2 | 0.8 | |
| UF | | ~1.5 | 7 ± 2 | | Collect retentate |
| System wash | Formulation buffer | 1 system volume | 7 ± 2 if pooled with retentate | | Collect and pool with retentate if protein |
| Rinse | water | | | | |
| CIP | 0.5-1M NaOH | | | | |
| store | 0.1M NaOH | | | | |

The product was diluted to 5 mg/ml and sterile filtered. The filtered drug substance is filled into bottles and frozen.

Example 9—Fed Batch Cultivation Process for Alpha Mannosidase

After cell thaw, the cells were expanded in shake flasks, 10 L seed bioreactor and 50 L seed bioreactor before their transfer to a production bioreactor (250 L). At inoculation day of the production bioreactor, the cell density in the 50 L seed bioreactor was between 2 and 2.5 MVC/mL. The cells were inoculated in the production reactor from the seed bioreactor at a cell density of 0.5 MVC/mL so that the cell suspension volume was 100 L when the inoculation was completed. Inoculation day is called day 0, the day after is called day 1, and so on. From day 1 to the end of the run, feed medium was added daily in boost according to a predefined rate (see below). From day 1 to the end of the run, glutamine and glucose were added daily in boost according to predefined rates and rules (see below). When the viable cell density >2.2 MVC/mL or at day 3, whatever came first, the temperature was decreased to the production temperature

TABLE 12

Actual temperatures and experimental conditions.

| | |
|---|---|
| DO (%) | 40 ± 5 |
| pH day 0 to day 2 (*) | between 6.60 and 6.95 |
| pH day 3 to end | 6.9 ± 0.05 |
| Temperature (° C.) A) → shifted to B) when the temperature shift condition is fulfilled | A) 36.5 ± 0.5<br>→ B) 31.0 ± 0.5 |
| Temperature shift condition | Cv ≥2.2 MVC/mL or day 3 (whatever comes first) |
| Agitation rate (rpm) to be adjusted according previous experience of the production bioreactor | suggestion: 45 rpm, shear stress tolerance of the cells supposed to be normal for CHO cells at 31° C. (not tested) |
| Inoculation viable cell density, (MVC/mL), at day 0 | 0.5 ± 0.1 |
| Max pCO$_2$ in liquid phase level | not known, tentatively 18 kPa |
| Feed of feed medium, glutamine and glucose | See text below |
| Glucose target in culture (mM) | 6 [5.5 9.0] |
| Glutamine target in culture (mM) | 2 mM D1-D3, 1 mM D4 and forward |
| Harvest condition | day 18-21 or viability <65%, whatever comes first |
| Working volume (L): initial → final | 100 → about 200 |
| Alkali added for pH control | 0.5M Na$_2$CO$_3$ |
| Dilution of inoculate cell broth from seed bioreactor to production bioreactor after completion of inoculation larger than | 4 |
| Criteria of the expanded cells in the seed bioreactor at the inoculation of the production bioreactor | |
| Minimal cell density (MVC/mL) | 2.0 |
| Maximal cell density (MVC/mL) | 2.5 |
| Number of millions viable cells | 44 to 56 |
| Viability | ≥93% |
| Batch cultivation in seed bioreactor 50 L before inoculation of production bioreactor not longer than (hours) | 76 |

(*) Between day 0 and day 2, only CO$_2$ was automatically added by pH control. Alkali was not added unless pH would be <6.60.

Base Medium

ACF medium (ExCell302, SAFC) supplemented with 2 mM glutamine and containing 11.1 mM (2 g/L) glucose. The base medium without glutamine can be transferred into the production bioreactor up to 3 days and stored at 36.5° C. i.e. during the sterility test of the bioreactor. Otherwise, the medium is stored at 4° C.

Feed Media

The feed medium, E35, was 35% CHO CD Efficient Feed B (InVitrogen cat nr. SKU# A10240-01) feed concentrate diluted in ACF medium without glutamine and containing 11.1 mM glucose. Feed medium was stored dark at 4° C. The feed medium can stand dark during up to 96 hours, i.e. four days, at room temperature during the cultivation.

TABLE 13

Feed medium volume added per day

| | Days | | |
|---|---|---|---|
| | 0 | 1 to 5 | 6 to 16 |
| Volume added/day in (L) | 0 | 12 | 4 |

Additives a) Stock solution of 2500 mM glucose. b) Stock solution of 200 mM glutamine. c) Alkali 0.5M Na$_2$CO$_3$.

Delivery of Feed Medium, Glucose and Glutamine

Feed medium was pumped daily in boost. Glucose and glutamine were added daily to maintain their concentrations within the given targets by adding, in boost, stock solutions of glucose and glutamine in amounts according to below.

Glutamine Addition Rules:

Day 1 to day 3: add a volume of glutamine stock solution so that the glutamine concentration in the bioreactor is 2 mM.

From day 4: add a volume of glutamine stock solution so that the glutamine concentration in the bioreactor is 1 mM.

Glucose Addition Rules:

Day 0 to day 8: no addition of glucose stock solution

From day 9, if glucose concentration in production bioreactor ≤8 mM, add a volume of glucose stock solution so that the glucose concentration in the bioreactor is 8 mM.

Process Overview:

TABLE 14

Day by day overview of cultivation process:

| Day | Action |
|---|---|
| −3 or −2 | Sterilization of the bioreactor and filling with ACF medium without or glutamine in volume 75 L or minimal volume to cover the probes (in case this is larger than 75 L)<br>Calibration of DO probe |

TABLE 14-continued

Day by day overview of cultivation process:

| Day | Action |
|---|---|
| 0 | a) Cell count of expanded cells in exponential growth from 50 L seed bioreactor and fulfilment of criteria for inoculation<br>b) Removal of ACF medium from production bioreactor if volume is >75 L. Stabilization of medium in production bioreactor at pH and temperature set points during at last 45 min and addition of glutamine to obtain a final glutamine concentration of 2 mM in 100 L medium. The glutamine present in the cell broth from the 50 L seed bioreactor is not taken into account.<br>c) Transfer of cell broth from 50 L seed bioreactor to production bioreactor<br>d) Adjustment of volume to 100 L cell suspension in production bioreactor<br>e) Stabilization for ≈1 hr (between 45' and 2 hrs 30') and sample for cell count, pH and metabolism parameters |
| 1 to 2 | Cell count, sample, feed of feed medium, feed of glucose and glutamine<br>pH controlled between 6.60 and 6.95 with automatic addition of CO2 (avoid alkali addition) |
| 3 | Cell count, sample, feed of feed medium, feed of glucose and glutamine<br>pH controlled at set point 6.9 ± 0.05 with automatic addition of alkali or $CO_2$<br>Decrease of temperature to 31° C. when either:<br>1) The viable cell density has reached 2.2 MVC/mL or<br>2) On day 3 |
| 4 to 17 | Cell count, sample, feed of respective feed media, feed of glucose and glutamine |
| 18-21 or viability <65% | Harvest |

Example 10—Characterization of the Purified Product Comprising Alpha-Mannosidase Table 15 below shows how the purification scheme of the present invention provided alpha-mannosidase with a high proportion of the 130 kDa glycoprotein species, as compared to the breakdown products of 75 and 55 kDa respectively. It is also shown how a 250 L process using a 4-step purification process with improved wash steps for both the capture step comprising multimodal ligands and the intermediate active step as well as a Q sepharose HP polishing step performed better than the 30 L process using a 3 step process with respect to both yield, overall purity and yield of the 130 kDa species.

TABLE 15

Yields of alpha-mannosidase species in purified product

| Purification Scale, method and purity | Percentages of individual alpha-mannosidase species after purification | | |
|---|---|---|---|
| | 130 kDa | 55 kDa | 75 kDa |
| 250\|4-step, 70% yield, purity = 99.6% | 95.2% | 1.5% | 2.9% |
| 30\|3-step, 60-70% yield, purity = 98.2% | 92.1% | 2.6% | 3.52% |

The distribution of species is seen in HPLC diagram of FIG. 7 for three processes, where the above represent the 4-step and 3-step processes respectively. The 2-step process shown is without using a multimodal ligand step. The first peak from the left is the 55 kDa species, followed by the 130 kDa and 75 kDa species respectively.

REFERENCES

Hirsch et al. EMBO J. 22, 1036-1046, 2003 and Saint-Pol et al. J. Biol. Chem. 274, 13547-13555, 1999
Aronson and Kuranda FASEB J 3:2615-2622. 1989
Nilssen et al. Hum. Mol. Genet. 6, 717-726. 1997
Kaneda et al. Chromosoma 95:8-12. 1987
Riise et al. Genomics 42:200-207, 1997
Nilssen et al. Hum. Mol. Genet. 6, 717-726. 1997
Liao et al. J. Biol. Chem. 271, 28348-28358. 1996
Nebes et al. Biochem. Biophys. Res. Commun. 200, 239-245. 1994
Chester et al., In: Durand P, O'Brian 3 (eds) Genetic errors of glycoprotein metabolism. Edi-Ermes, Milan, pp 89-120. 1982
Thomas and Beaudet. In: Scriver C R, Beaudet A L, Sly W A, Valle D (eds) The metabolic and molecular bases of inherited disease. Vol 5. McGraw-Hill, New York, pp 2529-2562. 1995
Hocking et al. Biochem J 128:69-78. 1972
Walkley et al. Proc. Nat. Acad. Sci. 91: 2970-2974, 1994
Crawley et al. Pediatr Res 46: 501-509, 1999
Stinchi et al. Hum Mol Genet 8: 1366-72, 1999
Berg et al. Biochem J. 328:863-870. 1997
Tollersrud et al. Eur J Biochem 246:410-419. 1997
Walkley et al. Proc. Nat. Acad. Sci. 91: 2970-2974, 1994
Will et al. Arch Dis Child 1987 October; 62(10):1044-9
Barton et al. N Engl J Med 324:1464-1470
Prows et al. Am J Med Genet 71:16-21
Neufeld, E. F. Enzyme replacement therapy, in "Lysosomal disorders of the brain" (Platt, F. M. Walkley, S. V: eds Oxford University Press).
Grubb et al. PNAS 2008, 105(7) pp. 2616-2621
Roces et al. Human Molecular Genetics 2004, 13(18) pp. 1979-1988
Blanz et al. Human Molecular Genetics 2008, 17(22) pp. 3437-3445
WO 02/099092
WO 05/094874
WO 05/077093
Berg et al. Molecular Genetics and Metabolism, 73, pp 18-29, 2001
Heikinheimo et al. J. Mol. Biol. 327, 631-644, 2003
Hansen et al., Biochem. J. (2004), 381, pp. 537-567

What is claimed is:

1. A composition comprising purified recombinant human lysosomal alpha-mannosidase, wherein at least 80% of the alpha-mannosidase is present as a 130 kDa recombinant human lysosomal alpha-mannosidase glycoprotein.

2. The composition of claim 1, wherein the recombinant human lysosomal alpha-mannosidase comprises a sequence selected from:
   a) a sequence set forth in SEQ ID NO: 2; or
   b) a sequence having at least 90% sequence identity to SEQ ID NO: 2, wherein said sequence has lysosomal alpha-mannosidase activity.

3. The composition of claim 1, wherein the recombinant human lysosomal alpha-mannosidase is obtained from a cell culture.

4. The composition of claim 3, wherein the cell culture is a fed-batch or a continuous cell culture.

5. The composition of claim 4, wherein the cell culture is prepared by:
   a) inoculating a production reactor comprising a base medium with cells capable of producing recombinant human lysosomal alpha-mannosidase on day 0, to provide a cell culture;
   b) adding a feed medium to said cell culture at least once from day 1; and
   c) adjusting the temperature of said cell culture to 35° C., 34° C., 33° C., 32° C., or 31° C., either after day 3 or when the viable cell density is higher than $2.1 \times 10^6$ viable cells/mL, whichever comes first.

6. The composition of claim 3, wherein said recombinant human lysosomal alpha-mannosidase is obtained by subjecting a fraction of said cell culture to chromatography on a resin comprising a multimodal ligand.

7. The composition of claim 6, wherein said fraction of said cell culture comprising the recombinant human lysosomal alpha-mannosidase is free of non-dissolved material or solids.

8. The composition of claim 1, wherein the composition is formulated in a formulation buffer comprising $Na_2HPO_4$, $NaH_2PO_4$, glycine, and mannitol.

9. The composition of claim 1, wherein the composition is formulated as an isotonic solution in a formulation buffer comprising 3.50 mM $Na_2HPO_4$, 0.17 mM $NaH_2PO_4$, 27 mM glycine, and 250 mM mannitol at a pH of 7.70.

10. A method of treating alpha-mannosidosis or reducing or alleviating the symptoms associated with alpha-mannosidosis, said method comprising administering to a subject in need thereof the composition of claim 2.

11. The method of claim 10, wherein the composition is formulated in a formulation buffer comprising $Na_2HPO_4$, $NaH_2PO_4$, glycine, and mannitol.

12. The method of claim 10, wherein the composition is formulated as an isotonic solution in a formulation buffer comprising 3.50 mM $Na_2HPO_4$, 0.17 mM $NaH_2PO_4$, 27 mM glycine, and 250 mM mannitol at a pH of 7.70.

13. A method of treating alpha-mannosidosis and/or reducing or alleviating the symptoms associated with alpha-mannosidosis, said method comprising administering to a subject in need thereof the composition of claim 1.

* * * * *